US012728279B2

(12) United States Patent
Ishikawa

(10) Patent No.: US 12,728,279 B2
(45) Date of Patent: Sep. 8, 2026

(54) PHOTOTHERAPY PLANNING DEVICE AND PHOTOTHERAPY PLANNING METHOD

(71) Applicant: Shimadzu Corporation, Kyoto (JP)

(72) Inventor: Akihiro Ishikawa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 18/286,358

(22) PCT Filed: Aug. 17, 2021

(86) PCT No.: PCT/JP2021/030080

§ 371 (c)(1),
(2) Date: Oct. 10, 2023

(87) PCT Pub. No.: WO2023/021581

PCT Pub. Date: Feb. 23, 2023

(65) Prior Publication Data

US 2024/0198124 A1 Jun. 20, 2024

(51) Int. Cl.
*A61N 5/06* (2006.01)
*A61B 1/00* (2006.01)

(52) U.S. Cl.
CPC .......... *A61N 5/06* (2013.01); *A61B 1/000094* (2022.02); *A61B 1/00045* (2013.01);
(Continued)

(58) Field of Classification Search
CPC .............. A61N 5/06; A61N 2005/0627; A61N 2005/0643; A61N 5/062;
(Continued)

(56) References Cited

U.S. PATENT DOCUMENTS

2010/0211136 A1* 8/2010 De Taboada ......... A61N 5/0617 607/88
2020/0197720 A1* 6/2020 Otsu .................... A61N 5/0603
2023/0027950 A1* 1/2023 Endo .................... A61B 90/361

FOREIGN PATENT DOCUMENTS

JP 2013236757 A * 11/2013
JP 2020-138940 A 9/2020
WO WO-2017169732 A1 * 10/2017 ............... G01C 3/06

OTHER PUBLICATIONS

Murakami (WO 2017169732) Measurement Device and Measurement Method machine translation (Year: 2017).*

(Continued)

*Primary Examiner* — Alexei Bykhovski
(74) *Attorney, Agent, or Firm* — Muir Patent Law, PLLC

(57) ABSTRACT

This phototherapy planning device is provided with a three-dimensional image acquisition unit configured to acquire a three-dimensional surface image showing an affected part of a subject, a rod-shaped member position adjustment unit configured to adjust a position of the rod-shaped member when inserting the rod-shaped member into the affected part on an image space, a light propagation region acquisition unit configured to acquire the light propagation region in which light propagates from the rod-shaped member, a cross-sectional image generation unit configured to generate a cross-sectional image that displays an internal morphological image including the affected part of the subject, the rod-shaped member, and the light propagation region, and a display control unit configured to perform control for displaying the cross-sectional image.

14 Claims, 11 Drawing Sheets

(52) U.S. Cl.
CPC ................ *A61N 2005/0627* (2013.01); *A61N 2005/0643* (2013.01)

(58) Field of Classification Search
CPC ...... A61N 2005/0612; A61N 2005/063; A61N 2005/0659; A61B 1/000094; A61B 1/00045; A61B 2034/107
See application file for complete search history.

(56) References Cited

OTHER PUBLICATIONS

Hasnine (JP 2013236757) Surgery Supporting Device machine translation (Year: 2013).*
Written Opinion by the International Searching Authority for PCT application No. PCT/JP2021/030080 dated Sep. 21, 2021.

* cited by examiner (A) Cross-sectional image (coronal cross section)

(B) Cross-sectional image (axial cross-section)

(C) Cross-sectional image (sagittal cross section)

23
50a
50b
50c
40
Degree of superposition of the first superimposed region : 70%
41
Degree of superposition of the second superimposed region : 10%

PHOTOTHERAPY PLANNING DEVICE AND PHOTOTHERAPY PLANNING METHOD

TECHNICAL FIELD

The present invention relates to a phototherapy planning device and a phototherapy planning method, more specifically to a phototherapy planning device and a phototherapy planning method for performing treatment planning when performing treatment by inserting a rod-shaped member into a subject and emitting light from the inserted rod-shaped member.

BACKGROUND ART

Conventionally, there are known a phototherapy planning device and a phototherapy planning method for performing treatment planning when performing treatment by inserting a rod-shaped member into a subject and emitting light from the inserted rod-shaped member. Such a phototherapy planning device and a phototherapy planning method are disclosed, for example, in Japanese Unexamined Patent Application Publication No. 2020-138940.

In Japanese Unexamined Patent Application Publication No. 2020-138940, a phototherapy device is disclosed in which a hollow needle is percutaneously inserted into a tumor or in the vicinity of the tumor to thereby place an optical fiber in the tumor or in the vicinity of the tumor through the needle, and light is emitted from a light diffusion portion located at the tip of the optical fiber to the tumor to perform the treatment of the tumor. In other words, Japanese Unexamined Patent Application Publication No. 2020-138940 discloses a phototherapy device for performing treatment by inserting a light diffusing portion (rod-shaped member) into a subject and emitting light from the inserted light diffusing portion. Further, Japanese Unexamined Patent Application Publication No. 2020-138940 discloses a configuration in which an operator punctures a needle while confirming an ultrasonic image when percutaneously puncturing the needle. Note that in the configuration disclosed in Japanese Unexamined Patent Application Publication No. 2020-138940, the tip of the needle and the light diffusing portion located at the tip of the optical fiber are arranged approximately at the same position.

PRIOR ART DOCUMENT

Patent Document

Patent Document 1: Japanese Unexamined Patent Application Publication No. 2020-138940

SUMMARY OF THE INVENTION

Problems to be Solved by the Invention

Here, the ultrasonic image is small in contrast difference between a tumor (affected part) and the surroundings of the affected part, and therefore, it is difficult to distinguish the affected part from parts other than the affected part. For this reason, as disclosed in Japanese Unexamined Patent Application Publication No. 2020-138940, in the case of confirming the placement of the light diffusing portion (rod-shaped member) located at the tip of the optical fiber while confirming the placement of the tip of the needle using the ultrasonic image, there is an inconvenience that it is difficult for the operator to accurately determine whether the placement of the rod-shaped member with respect to the affected part is correct. Furthermore, as disclosed in Japanese Unexamined Patent Application Publication No. 2020-138940, in the case of performing needle puncture (insertion) while confirming an ultrasonic image, it is only possible to confirm the affected part immediately before the insertion, and therefore, there is an inconvenience that the irradiation range of the therapeutic light to be emitted to the affected part cannot be grasped in advance. Therefore, there are problems that it is difficult to accurately grasp the placement of the rod-shaped member with respect to the affected part and grasp in advance the irradiation range of the therapeutic light with respect to the affected part.

The present invention has been made to solve the above-described problems, and one object of the present invention is to provide a phototherapy planning device and a phototherapy planning method capable of accurately grasping a placement of a rod-shaped member with respect to an affected part and also capable of grasping in advance an irradiation range of therapeutic light with respect to the affected part.

Means for Solving the Problems

In order to attain the above-described objects, a phototherapy planning device according to a first aspect of the present invention includes:

- a three-dimensional image acquisition unit configured to acquire a three-dimensional surface image showing an affected part of a subject and a three-dimensional surface shape of the subject;
- a rod-shaped member position adjustment unit configured to adjust a position of a rod-shaped member when inserting the rod-shaped member into the affected part on an image space, with respect to the three-dimensional surface image;
- a light propagation region acquisition unit configured to acquire a light propagation region in which light propagates from the rod-shaped member;
- a cross-sectional image generation unit configured to generate a cross-sectional image that displays, in a predetermined cross-section of the three-dimensional surface image, an internal morphological image including the affected part of the subject, the rod-shaped member, and the light propagation region; and
- a display control unit configured to perform control for displaying the cross-sectional image.

Further, a phototherapy planning method according to a second aspect of the present invention includes:

- a step of acquiring a three-dimensional surface image showing an affected part of a subject and a three-dimensional surface shape of the subject;
- a step of adjusting a position of a rod-shaped member when inserting the rod-shaped member into the affected part on an image space, with respect to the three-dimensional surface image;
- a step of acquiring a light propagation region in which light propagates from the rod-shaped member;
- a step of generating a cross-sectional image that displays, in a predetermined cross-section of the three-dimensional surface image, an internal morphological image including the affected part of the subject, the rod-shaped member, and the light propagation region; and
- a step of causing the cross-sectional image to be displayed.

Effects of the Invention

In the phototherapy planning device according to the first aspect of the present invention, as described above, it is provided with a rod-shaped member position adjustment unit for adjusting the position of the rod-shaped member when inserting the rod-shaped member into the affected part on the image space with respect to the three-dimensional surface image. With this, since it is possible to perform the position adjustment of the rod-shaped member on the image space of the three-dimensional surface image showing the affected part, the operator can perform the position adjustment of the rod-shaped member while confirming the rod-shaped member on the image space of the three-dimensional surface image. Further, it is provided with the light propagation region acquisition unit for acquiring the light propagation region in which light propagates from the rod-shaped member, the cross-sectional image generation unit for generating a cross-sectional image displaying an internal morphological image including the affected part of the subject, the rod-shaped member, and the light propagation region in a predetermined cross section of the three-dimensional surface image, and the display control unit for performing control to cause the cross-sectional image to be displayed. Therefore, it is possible for the operator to grasp in advance the light propagation region, which is the region of the light emitted from the rod-shaped member, by confirming the internal morphological image including the affected part of the subject and the cross-sectional image displaying the rod-shaped member, and the light propagation region. As a result, it is possible to provide a phototherapy planning device capable of accurately grasping the placement of the rod-shaped member with respect to the affected part and also capable of grasping in advance the irradiation range of the therapeutic light to the affected part.

Further, in the phototherapy planning method according to the second aspect of the present invention, it is provided with: a step of adjusting a position of the rod-shaped member when inserting the rod-shaped member into the affected part on an image space with respect to the three-dimensional surface image; a step of acquiring the light propagation region in which light propagates from the rod-shaped member; a step of generating a cross-sectional image that displays, in a predetermined cross-section of the three-dimensional surface image, an internal morphological image including the affected part of the subject, the rod-shaped member, and the light propagation region; and a step of causing the cross-sectional image to be displayed. With this, it possible to provide a phototherapy planning method, in the same manner as the phototherapy planning device according to the first aspect, capable of accurately grasping the placement of the rod-shaped member with respect to the affected part and also capable of grasping in advance the irradiation range of the therapeutic light with respect to the affected part.

EMBODIMENTS FOR CARRYING OUT THE INVENTION

Hereinafter, some embodiments in which the present invention is embodied will be described based on the attached drawings.

With reference to FIG. 1 to FIG. 9, the configuration of the phototherapy planning device according to one embodiment will be described. The phototherapy planning device 100 is a device for performing treatment planning of near-infrared photoimmunotherapy (NIR-PIT). In near-infrared photoimmunotherapy, a medicine in which a photosensitive substance (e.g., IRDye (registered trademark) 700Dx), which emits fluorescence when it absorbs therapeutic light, and an antibody (e.g., an antibody to the epidermal growth factor receptor), which selectively binds to a tumor, is first administered to a subject by intravenous infusion or other means. Then, in order to allow the medicine to circulate throughout the entire body of the subject, it is allowed to elapse, for example, one day (24 hours) from the administration of the medicine to the subject. During this period of time, the antibody of the medicine administered to the subject selectively binds to the tumor. This results in a photochemical reaction, changing the chemical structure of the photosensitive substance. This change in the chemical structure of the photosensitive substance causes a change in the steric structure of the antibody. The change in the steric structure of the antibody bound to the tumor then causes damage to the cell membrane of the bound tumor. As a result, the tumor is swollen and ruptured by water that has penetrated through the damaged portions of the membrane of the tumor, thereby destroying (killing) the tumor. In this embodiment, the phototherapy planning device 100 performs treatment planning by a method in which an affected part 90 (see FIG. 3) is irradiated with therapeutic light in a state in which a probe is punctured into the subject.

(Configuration of Phototherapy Planning Device)

Figure 1:
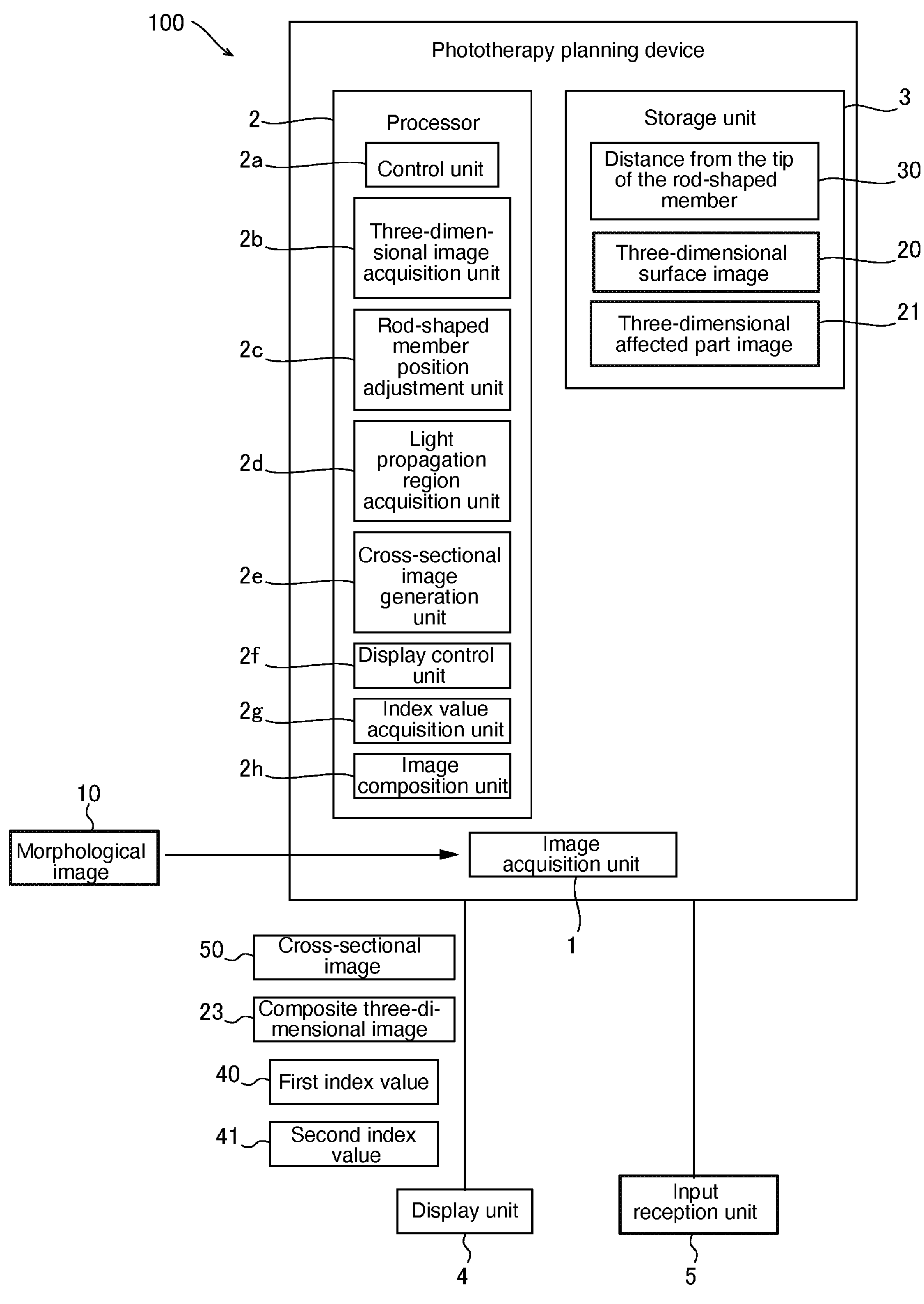
FIG. 1 is a block diagram showing an entire configuration of a phototherapy planning device according to one embodiment.

As shown in FIG. 1, the phototherapy planning device 100 of this embodiment is provided with an image acquisition unit 1, a processor 2, a storage unit 3, a display unit 4, and an input reception unit 5.

The image acquisition unit 1 is configured to acquire a morphological image 10. The morphological image 10 is an image displaying a region including the affected part 90 (see FIG. 3) of the subject. In this embodiment, the image acquisition unit 1 is configured to acquire a plurality of morphological images 10. The image acquisition unit 1 includes, for example, an input/output interface. Note that the morphological image 10 includes, e.g., an MRI (Magnetic Resonance Image) image, or a CT (Computed Tomography) image.

The processor 2 is configured to generate a cross-sectional image 50 based on the acquired morphological image 10. The processor 2 includes, e.g., a CPU (Central Processing Unit), a ROM (Read Only Memory), a RAM (Random Access Memory), a GPU (Graphics Processing Unit), or an FPGA (Field-Programmable Gate Array) configured for image processing, or an FPGA (Field-Programmable Gate Array) configured for image processing. Further, the processor 2 composed of a CPU as hardware is provided with, as functional blocks of software (programs), a control unit 2*a*, a three-dimensional image acquisition unit 2*b*, a rod-shaped member position adjustment unit 2*c*, a light propagation region acquisition unit 2*d*, a cross-sectional image generation unit 2*e*, and a display control unit 2*f*. Further, in this embodiment, the processor 2 includes, as a software (program) functional block, an index value acquisition unit 2*g*. Further, in this embodiment, the processor 2 includes, as a software (program) functional block, an image composition unit 2*h*.

By executing the programs stored in the storage unit 3, the processor 2 functions as the control unit 2*a*, the three-dimensional image acquisition unit 2*b*, the rod-shaped member position adjustment unit 2*c*, the light propagation region acquisition unit 2*d*, the cross-sectional image generation unit 2*e*, the display control unit 2*f*, the index value acquisition unit 2*g*, and the image composition unit 2*h*. The control unit 2*a*, the three-dimensional image acquisition unit 2*b*, the rod-shaped member position adjustment unit 2*c*, the light propagation region acquisition unit 2*d*, the cross-sectional image generation unit 2*e*, the display control unit 2*f*, the index value acquisition unit 2*g*, and the image composition unit 2*h* may be individually configured by hardware with a dedicated processor (processing circuit).

The control unit 2*a* is configured to control the phototherapy planning device 100.

The three-dimensional image acquisition unit 2*b* is configured to acquire a three-dimensional surface image 20 (see FIG. 2) showing the affected part 90 (see FIG. 3) of the subject as well as the three-dimensional surface shape of the subject. In this embodiment, the three-dimensional image acquisition unit 2*b* is configured to acquire a three-dimensional affected part image 21 (see FIG. 3), which is a three-dimensional image of the affected part 90. Further, in this embodiment, by superimposing the three-dimensional surface image 20 and the three-dimensional affected part image 21, it becomes a state in which the affected part 90 is visible in the three-dimensional surface image 20. The configuration that the three-dimensional image acquisition unit 2*b* acquires the three-dimensional surface image 20 and the configuration that the three-dimensional image acquisition unit 2*b* acquires the three-dimensional affected part image 21 are detailed below.

The rod-shaped member position adjustment unit 2*c* is configured to adjust the position of the rod-shaped member 6 when inserting the rod-shaped member 6 (see FIG. 4) into the affected part 90 on the image space with respect to the three-dimensional surface image 20. Note that the image space is a three-dimensional space in which the three-dimensional surface image 20 is displayed. The rod-shaped member 6 includes a light diffusing member (diffuser) provided at the tip of an optical fiber to irradiate an affected part 90 of a subject with light (therapeutic light). The configuration that the rod-shaped member position adjustment unit 2*c* adjusts the position of the rod-shaped member 6 will be detailed below.

The light propagation region acquisition unit 2*d* is configured to acquire a light propagation region 31 (see FIG. 5) in which light propagates from the rod-shaped member 6. The configuration that the light propagation region acquisition unit 2*d* acquires the light propagation region 31 are detailed below.

The cross-sectional image generation unit 2*e* is configured to generate a cross-sectional image 50 that displays, in a given cross-section of the three-dimensional surface image 20, an internal morphological image 60 (see FIG. 5) including the affected part 90 of the subject, the rod-shaped member 6, and the light propagation region 31. The internal morphological image 60 is an image in which the internal structure including the affected part 90 of the subject is displayed. The internal structure includes, for example, the brain of the subject. The configuration that the cross-sectional image generation unit 2*e* generates the cross-sectional image 50 is detailed below.

The display control unit 2*f* is configured to perform control for displaying the cross-sectional image 50. In this embodiment, the display control unit 2*f* is configured to perform control for displaying the cross-sectional image 50 on the display unit 4.

The index value acquisition unit 2*g* is configured to acquire a first index value 40 which is an index value indicating how much the affected part 90 is irradiated with the therapeutic light. Further, the index value acquisition unit 2*g* is configured to acquire a second index value 41 which is an index value indicating how much a part other than the affected part 90 is irradiated with the therapeutic light. The configuration that the index value acquisition unit 2*g* acquires the first index value 40 and the second index value 41 will be detailed below.

Figure 2:
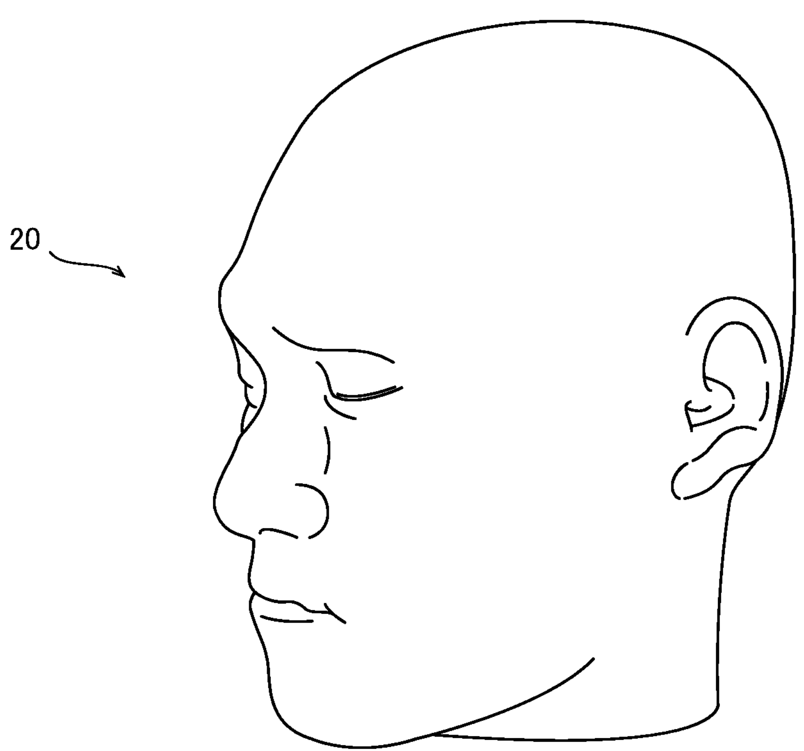
FIG. 2 is a schematic diagram for describing a three-dimensional surface image acquired by a three-dimensional image acquisition unit according to one embodiment.

In this embodiment, initially, the three-dimensional image acquisition unit 2*b* acquires a three-dimensional surface image 20 (see FIG. 2). Further, the three-dimensional image acquisition unit 2*b* acquires a three-dimensional affected part image 21 (see FIG. 3). The image composition unit 2*h* then composes the three-dimensional surface image 20 and the three-dimensional affected part image 21 to generate a composite three-dimensional image 22. Thereafter, the display control unit 2*f* makes the display unit 4 display the composite three-dimensional image 22. After completion of the position adjustment of the rod-shaped member 6 by the operator, the cross-sectional image generation unit 2*e* generates a plurality of cross-sectional images 50 (see FIG. 5). Further, the image composition unit 2*h* superimposes a plurality of cross-sectional images 50 on the composite three-dimensional image 22 to thereby generate a composite three-dimensional image 23. Thereafter, the display control unit **2*f* makes the display unit 4 display the composite three-dimensional image 23 and a plurality of cross-sectional images 50**.

The image composition unit **2*h* is configured to compose the three-dimensional surface image 20 and the three-dimensional affected part image 21 to thereby generate a composite three-dimensional image 22 capable of identifying the three-dimensional affected part image 21. The configuration that the image composition unit 2*h* generates the composite three-dimensional image 22** will be detailed below.

The storage unit 3 is configured to store the distance 30 (see FIG. 5) from the tip **6*a* (see FIG. 5) of the rod-shaped member 6, which will be described later, the three-dimensional surface image 20, and the three-dimensional affected part image 21. The storage unit 3 is configured to store various programs to be executed by the processor 2. The storage unit 3** includes a storage device, such as, e.g., a hard disk drive (HDD) and a solid-state drive (SSD).

The display unit 4 is configured to display the cross-sectional images 50 generated by the cross-sectional image generation unit **2*e*, the composite three-dimensional image 23 generated by the image composition unit 2*h*, the first index value 40 and the second index value 41 acquired by the index value acquisition unit 2*g*, etc. The display unit 4** includes a display device, such as, e.g., an LCD monitor.

The input reception unit 5 is configured to receive an operation input of the operator. The input reception unit 5 includes an input device, such as, e.g., a mouse and a keyboard.

(Three-Dimensional Surface Image and Three-Dimensional Affected Part Image)

Figure 3:
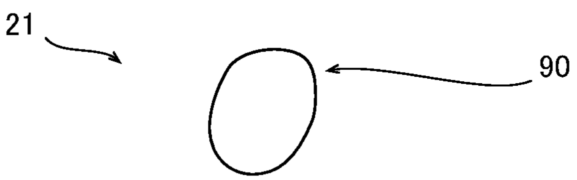
FIG. 3 is a schematic diagram for describing a three-dimensional affected part image acquired by a three-dimensional image acquisition unit according to one embodiment.

Referring to FIG. 2 and FIG. 3, the configuration that the three-dimensional image acquisition unit **2*b* acquires the three-dimensional surface image 20 and the three-dimensional affected part image 21** is described.

Initially, referring to FIG. 2, the configuration that the three-dimensional image acquisition unit **2*b* acquires the three-dimensional surface image 20** is described.

The three-dimensional image acquisition unit **2*b* acquires a three-dimensional surface image 20 based on a plurality of morphological images 10 acquired by the image acquisition unit 1. The morphological image 10 is a slice image of the head of the subject. In this embodiment, the three-dimensional image acquisition unit 2*b* performs surface rendering using the plurality of morphological images 10 to thereby acquire a three-dimensional surface image 20 showing the surface shape of the subject. In other words, the three-dimensional surface image 20 is an image in which the inside is hollow, the image showing the surface shape of the subject. Further, the control unit 2*a* is configured to move the three-dimensional surface image 20 to any position at any angle on the image space, based on the operator's operation input received by the input reception unit 5**.

Next, referring to FIG. 3, the configuration that the three-dimensional image acquisition unit **2*b* acquires the three-dimensional affected part image 21** is described.

The three-dimensional affected part image 21 shown in FIG. 3 is a three-dimensional image of the affected part 90. The three-dimensional image acquisition unit **2*b* acquires the three-dimensional affected part image based on a plurality of affected part slice images (not shown) each showing the affected part 90. The affected part slice image is acquired by deleting regions other than the affected part 90 from a plurality of slice images each showing the affected part 90 by the operator. Further, the control unit 2*a* is configured to move the three-dimensional affected part image 21 together with the three-dimensional surface image 20 to any position at any angle on the image space, based on the operator's operation input received by the input reception unit 5**.

(Composite Three-Dimensional Image)

Figure 4:
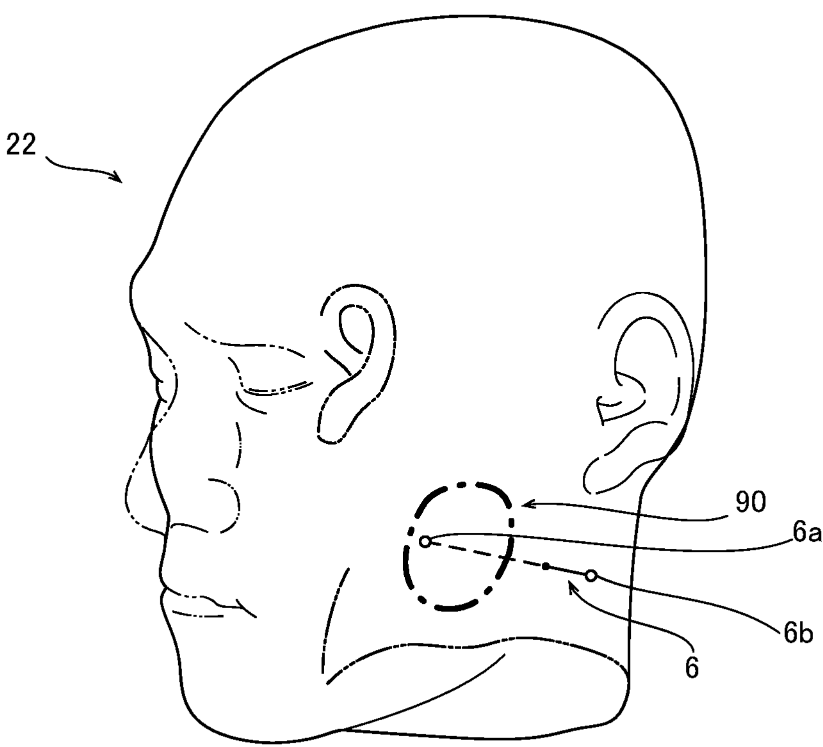
FIG. 4 is a schematic diagram for describing a three-dimensional image generated by an image composition unit according to one embodiment.

Next, referring to FIG. 4, the composite three-dimensional image 22 is described. The image composition unit **2*h* composes the three-dimensional surface image 20 and the three-dimensional affected part image 21 to thereby generate a composite three-dimensional image 22. Specifically, the image composition unit 2*h* superimposes the three-dimensional affected part image 21 on the three-dimensional surface image 20 to thereby generate a composite three-dimensional image 22. Note that the image composition unit 2*h* displays the three-dimensional surface image 20 and the three-dimensional affected part image 21 in the composite three-dimensional image 22 in a distinguishable manner. Specifically, the image composition unit 2*h* differentiates the display mode of the three-dimensional surface image 20 from that of the three-dimensional affected part image 21 to cause the three-dimensional surface image 20 and the three-dimensional affected part image 21 to be displayed in a distinguishable manner. In this embodiment, the image composition unit 2*h* highlights the border of the three-dimensional affected part image 21 to display the three-dimensional surface image 20 and the three-dimensional affected part image 21 in a distinguishable manner. In the example shown in FIG. 4, the three-dimensional affected part image 21 is illustrated with a bold, single-dashed line to indicate that the three-dimensional surface image 20 and the three-dimensional affected part image 21** can be distinguished.

(Position Adjustment of Rod-Shaped Member)

Further referring to FIG. 4, the configuration that the rod-shaped member position adjustment unit **2*c* performs the position adjustment of the rod-shaped member 6 will be described. Note that in this embodiment, although the position adjustments of a plurality of rod-shaped members 6 can be performed, the same configuration is used for the position adjustment of any one of the rod-shaped members 6, so the configuration for the position adjustment of a single rod-shaped member 6 is described as representative. Further, before performing the position adjustment of the rod-shaped member 6, the number of rod-shaped members 6 to be adjusted in position is input in advance by the operator and stored in the storage unit 3**.

In this embodiment, the rod-shaped member position adjustment unit **2*c* is configured to adjust the position of the rod-shaped member 6 on the image space based on the operation input received by the input reception unit 5. Specifically, the rod-shaped member position adjustment unit 2*c* adjusts the position of the rod-shaped member 6 by adjusting the position of the tip 6*a* of the rod-shaped member 6 and the position of the end 6*b* opposite the tip 6*a*, based on the operation input received by the input reception unit 5. In other words, the rod-shaped member position adjustment unit 2*c* adjusts the position of the tip 6*a* of the rod-shaped member 6 and that of the end 6*b* of the rod-shaped member 6 opposite to the tip 6*a* to thereby adjust the insertion angle and the depth of the rod-shaped member 6. Specifically, when the operator performs the position adjustment, the rod-shaped member position adjustment unit 2*c* acquires the position coordinate of the tip 6*a* and the position coordinate of the end 6*b* opposite the tip 6*a*. In other words, the rod-shaped member position adjustment unit 2*c* acquires the insertion angle and the depth of the rod-shaped member 6 based on the position coordinate of the tip 6***a* and the position coordinate of the end 6*b* opposite to the tip 6*a*.

(Cross-Sectional Image)

Figure 5:
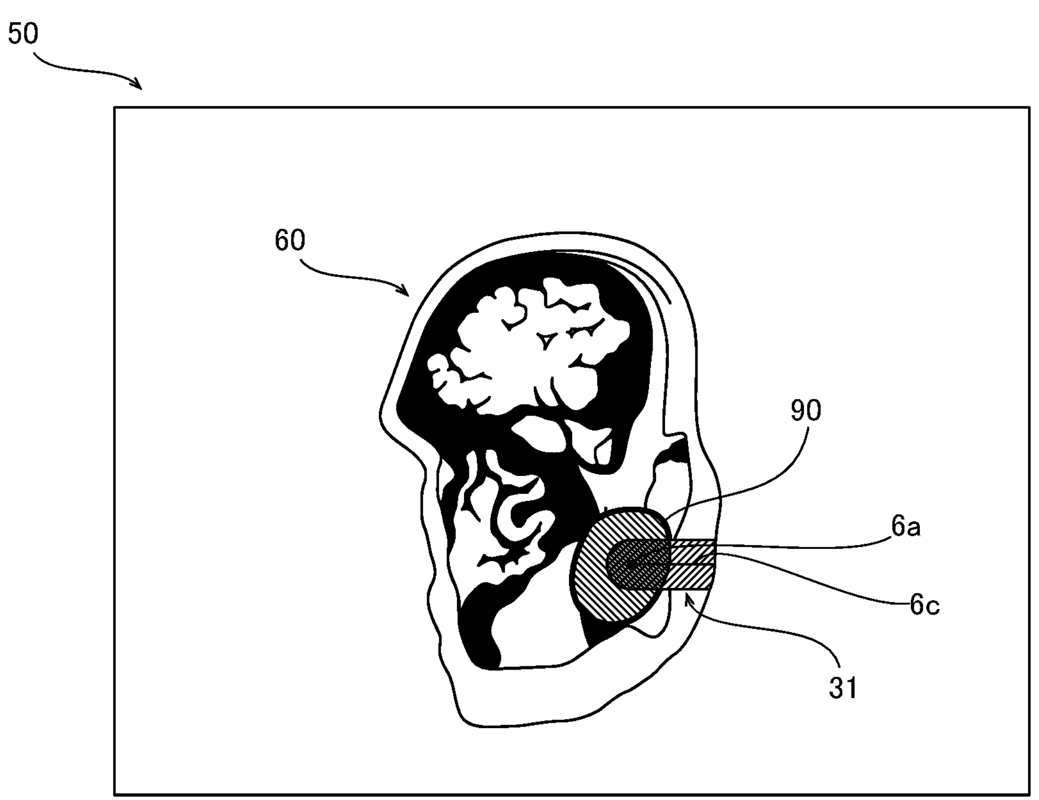
FIG. 5 is a schematic diagram for describing a cross-sectional image generated by a cross-sectional image generation unit according to one embodiment.

Next, referring to FIG. 5, the cross-sectional image 50 is described. The cross-sectional image generation unit 2*e* is configured to generate a cross-sectional image 50 of the cross-section where the rod-shaped member 6 is positioned in the three-dimensional surface image 20. In this embodiment, the cross-sectional image generation unit 2*e* is configured to generate the cross-sectional image 50 after completing the position adjustments of the plurality of rod-shaped members 6. In other words, when displaying the composite three-dimensional image 22 on the display unit 4, the cross-sectional image generation unit 2*e* does not reconstruct the internal morphological image 60 but reconstructs the internal morphological image 60 in the cross-section where the rod-shaped member 6 is positioned when completing the position adjustment of the rod-shaped member 6.

Further, in this embodiment, the cross-sectional image generation unit 2*e* generates an image capable of identifying the light propagation region 31, as the cross-sectional image 50. As shown in FIG. 5, in this embodiment, the cross-sectional image generation unit 2*e* differentiates the display mode of the light propagation region 31 from the display mode of the affected part 90 to display the light propagation region 31 and the affected part 90 in a distinguishable manner. Specifically, the cross-sectional image generation unit 2*e* differentiates the display color of the light propagation region 31 from the display color of the affected part 90 to display the affected part 90 and the light propagation region 31 in a distinguishable manner. In the example shown in FIG. 5, each of the first superimposed region 80 and the second superimposed region 82 is differentiated in hatching from the affected part 90 in the cross-sectional image 50, so that the light propagation region 31 is displayed in an identifiable manner.

Further, as shown in FIG. 5, in this embodiment, the cross-sectional image generation unit 2*e* is configured to generate, as the cross-sectional image 50, an image capable of distinguishing the affected part 90 from other parts of the body other than the affected part 90. Specifically, the cross-sectional image generation unit 2*e* differentiates the display mode of the affected part 90 from the display mode of other parts other than the affected part 90, so that the affected part 90 and other parts other than the affected part 90 are displayed in a distinguishable manner. In the example shown in FIG. 5, the display color of the affected part 90 and the display color of other parts other than the affected part 90 are differentiated, so that the affected part 90 and other parts other than the affected part 90 are displayed in a distinguishable manner. In the example shown in FIG. 5, the border of the affected part 90 is illustrated with a bold line, and the affected part 90 is hatched to indicate that the affected part 90 can be distinguished from other parts of the body other than the affected part 90.

(Light Propagation Region)

Figure 6:
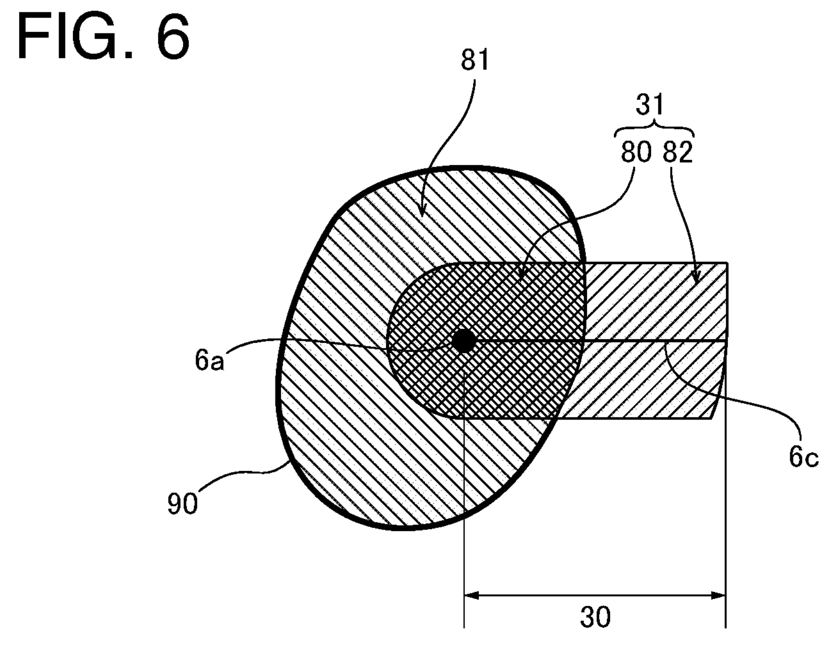
FIG. 6 is a schematic diagram for describing a light propagation region, a first superimposed region, a non-superimposed region, and a second superimposed region.

Next, referring to FIG. 6, the configuration that the light propagation region acquisition unit 2*d* acquires the light propagation region 31 is described. FIG. 6 is an enlarged image showing the portion displaying the affected part 90 and the light propagation region 31 within the cross-sectional image 50 shown in FIG. 5. In this embodiment, the light propagation region acquisition unit 2*d* determines the light irradiation range in the rod-shaped member 6 based on the distance 30 from the tip 6*a* of the rod-shaped member 6 and the position of the tip 6*a* of the rod-shaped member 6. The light propagation region acquisition unit 2*d* is configured to acquire, as the light propagation region 31, the region in which the light emitted radially outward from the center of the shaft portion 6*c* of the rod-shaped member 6 inserted into the subject out of the rod-shaped member 6 over the entire circumference of the rod-shaped member 6 propagates. In other words, in this embodiment, the light propagation region acquisition unit 2*d* is configured to acquire the light propagation region 31 based on the distance 30 from the tip 6*a* of the rod-shaped member 6 input in advance and the position of the tip 6*a* of the rod-shaped member 6.

Here, it is known that, in general, the arrival range of light of the light quantity that can achieve therapeutic effects out of the light emitted radially outward from the center of the shaft portion 6*c* of the rod-shaped member 6 inserted in a subject is approximately 9 mm. Therefore, the light propagation region acquisition unit 2*d* acquires, as the light propagation region 31, the region from the center of the shaft portion 6*c* of the rod-shaped member 6 within a determined range to the distance of approximately 9 mm in the radially outward direction over the entire circumference of the rod-shaped member. Note that the distance 30 from the tip 6*a* of the rod-shaped member 6 is input in advance by the operator for each rod-shaped member 6. Further, in this embodiment, the control unit 2*a* is configured such that the distance 30 from the tip 6*a* of the rod-shaped member 6 can be input within a predetermined range. Specifically, the control unit 2*a* is configured such that the distance 30 from the tip 6*a* of the rod-shaped member 6 can be input within the range of 20 mm to 40 mm.

In this embodiment, the cross-sectional image generation unit 2*e* is configured to generate, as the cross-sectional image 50, an image capable of identifying the first superimposed region 80 in which the affected part 90 and the light propagation region 31 are superimposed and the non-superimposed region 81 other than the first superimposed region 80. The cross-sectional image generation unit 2*e* differentiates the display mode of the first superimposed region 80 from the display mode of the non-superimposed region 81 to display the first superimposed region 80 and the non-superimposed region 81 in a distinguishable manner. In the example shown in FIG. 6, the display color of the first superimposed region 80 is differentiated from the display color of the non-superimposed region 81 to generate an image capable of distinguishing the first superimposed region 80 from the non-superimposed region 81. In the example shown in FIG. 6, the first superimposed region 80 and the non-superimposed region 81 are hatched with different hatching to indicate that the first superimposed region 80 and the non-superimposed region 81 can be distinguished from each other. Note that the non-superimposed region 81 denotes a region not irradiated with therapeutic light within the affected parts 90.

Further, as shown in FIG. 6, the light propagation region 31 includes the first superimposed region 80 and the second superimposed region 82. The cross-sectional image generation unit 2*e* is configured to display the first superimposed region 80 and the second superimposed region 82 in an identifiable manner. Specifically, the cross-sectional image generation unit 2*e* differentiates the first superimposed region 80 from the second superimposed region 82 to display the first superimposed region 80 and the second superimposed region 82 in a distinguishable manner. In the example shown in FIG. 6, the cross-sectional image generation unit 2*e* differentiates the display color of the first superimposed region 80 from that of the second superimposed region 82 to display the first superimposed region 80 and the second superimposed region 82 in a distinguishable manner. Note that in the example shown in FIG. 6, the cross-sectional image generation unit 2*e* differentiates the display color of the first superimposed region 80 from that of the second superimposed region 82 to display the first superimposed region 80 and the second superimposed region 82 in a distinguishable manner. The second superimposed region 82 is a region that includes other parts other than the affected part 90 within the light propagation region 31.

(Cross-Sectional Images in Plurality of Cross-Sections)

Next, with reference to (A) to (C) of FIG. 7, a cross-sectional image 50*a* to a cross-sectional image 50*c* in a plurality of cross-sections will be described. The cross-sectional image generation unit 2*e* is configured to generate a plurality of cross-sectional images 50 showing at least the tip 6*a* of the rod-shaped member 6. Specifically, the cross-sectional image generation unit 2*e* is configured to generate three cross-sectional images 50*a* to 50*c*. More specifically, the cross-sectional image generation unit 2*e* is configured to generate a cross-sectional image 50*a* (see (A) of FIG. 7), which is an image of a cross-section perpendicular to the direction along the shaft portion 6*c* of the rod-shaped member 6. Hereafter, the cross section perpendicular to the direction along the shaft portion 6*c* of the rod-shaped member 6 is referred to as a coronal cross section.

Figure 7:
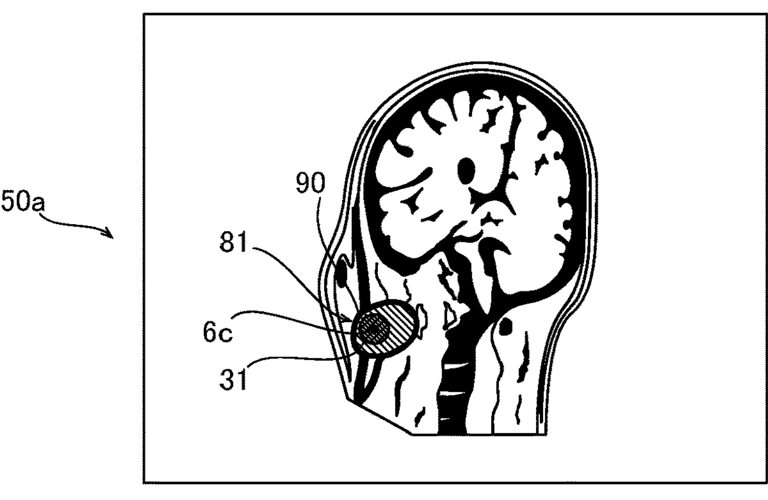
FIG. 7 shows schematic diagrams (A) to (C) for describing three cross-sectional images generated by a cross-sectional image generation unit according to one embodiment.
Figure 7:
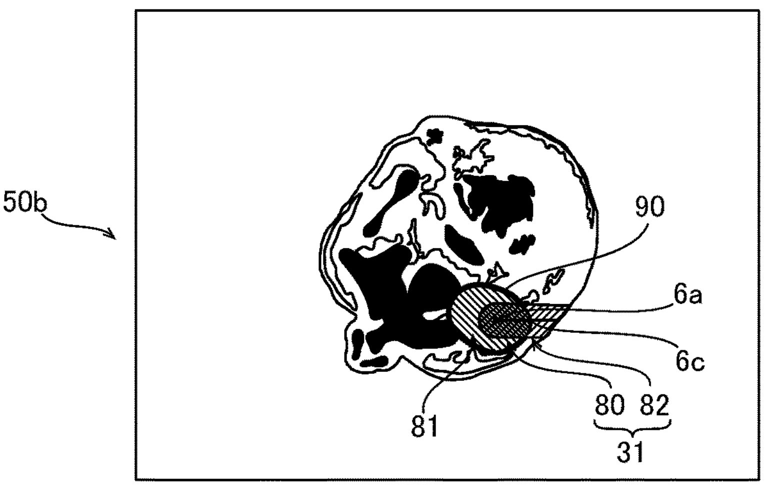
Figure 7:
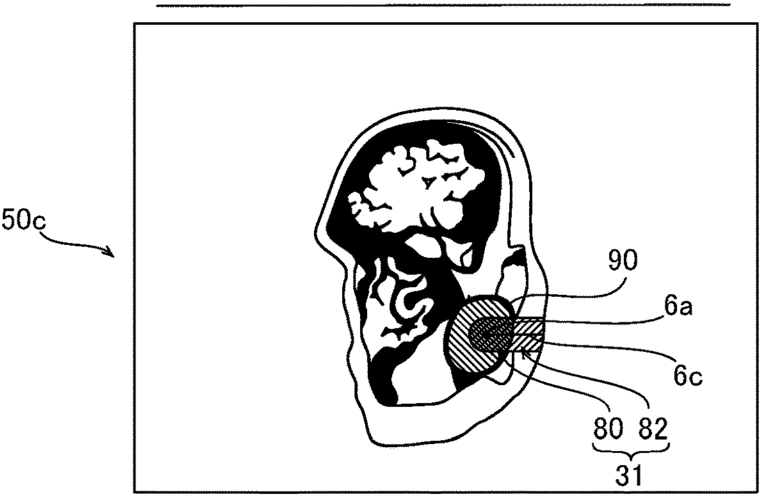

Further, the cross-sectional image generation unit 2*e* is configured to generate a cross-sectional image 50*b* (see (B) of FIG. 7), which is an image of the cross-section including the shaft portion 6*c* of the rod-shaped member 6 and the horizontal axis perpendicular to the shaft portion 6*c*. Hereafter, the cross section including the shaft portion 6*c* of the rod-shaped member 6 and the horizontal axis perpendicular to the shaft portion 6*c* is referred to as an axial cross section.

Further, the cross-sectional image generation unit 2*e* is configured to generate a cross-sectional image 50*c* (see (C) of FIG. 7), which is an image of the cross section including the shaft portion 6*c* of the rod-shaped member 6 and the vertical axis perpendicular to the shaft portion 6*c*. Hereafter, the cross section including the shaft portion 6*c* of the rod-shaped member 6 and the vertical axis perpendicular to the shaft portion 6*c* is referred to as a sagittal cross section.

The cross-sectional image 50*a* shown in (A) of FIG. 7 is a coronal cross section. In the cross-sectional image 50*a*, the affected part 90, other parts of the body other than the affected part 90, and the light propagation region 31 in the coronal cross section are displayed. In the example shown in (A) of FIG. 7, the light propagation region 31 is smaller than the affected part 90, so the first superimposed region 80 is displayed as the light propagation region 31.

The cross-sectional image 50*b* shown in (B) of FIG. 7 is an image of the axial cross section. In the cross-sectional image 50*b*, the affected part 90, other parts other than the affected part 90, the light propagation region 31, the non-superimposed region 81, and the second superimposed region 82 in the axial cross section are shown.

The cross-sectional image 50*c* shown in (C) of FIG. 7 is an image of a sagittal cross section. In the cross-sectional image 50*c*, the affected part 90, other parts other than the affected part 90, the light propagation region 31, the non-superimposed region 81, and the second superimposed region 82 in the sagittal cross section are shown. Note that the example shown in (C) of FIG. 7 is a cross-sectional image 50*c*, which is a sagittal cross-sectional image and is different from the cross-sectional image 50*b*, which is an image of the axial cross section, so that the affected part 90 is shown in a different shape.

(Composite Three-Dimensional Image in which Cross-Sectional Images are Superimposed)

Figure 8:
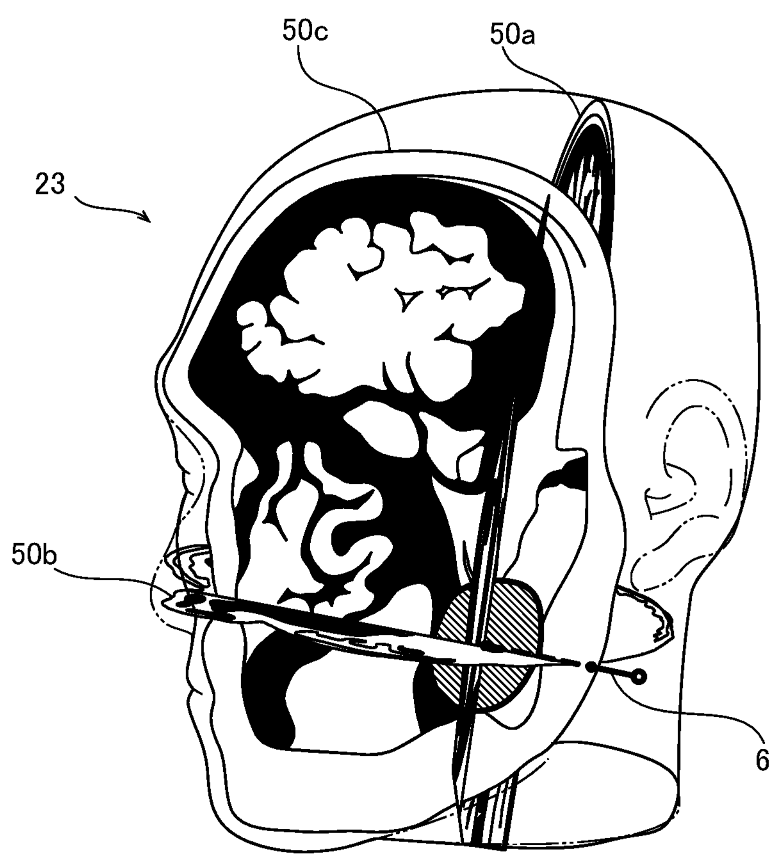
FIG. 8 is a schematic diagram for describing a composite three-dimensional image in which cross-sectional images generated by the image composition unit according to one embodiment are superimposed.

Next, referring to FIG. 8, the composite three-dimensional image 23 in which the cross-sectional images 50 are superimposed will be described. In this embodiment, the image composition unit 2*h* superimposes the cross-sectional images 50 to generate a composite three-dimensional image 23. Note that in this embodiment, the image composition unit 2*h* superimposes the cross-sectional image 50*a*, which is an image of a coronal cross section, the cross-sectional image 50*b*, which is an image of an axial cross section, and the cross-sectional image 50*c*, which is an image of a sagittal cross section image, on the composite three-dimensional image 22 (see FIG. 4) to thereby generate the composite three-dimensional image 23. Note that in the example shown in FIG. 8, although it is mainly illustrated at an angle from which the cross-sectional image 50*c* can be viewed, the cross-sectional image 50*a* or the cross-sectional image 50*b* can be visually recognized by changing the orientation of the composite three-dimensional image 23 on the image space by means of an operation input.

(First Index Value and Second Index Value)

Here, in photoimmunotherapy, a medicine containing a photosensitive substance is administered and the affected part 90 is irradiated with therapeutic light to perform the treatment of the affected part 90. In this case, in the case where the light quantity of the therapeutic light emitted to the affected part 90 is not sufficient, sufficient therapeutic effects cannot be obtained. Therefore, in this embodiment, the index value acquisition unit 2*g* is configured to acquire a first index value 40 (see FIG. 9) that indicates the degree of superposition of the first superimposed region 80 (see FIG. 5) with respect to the affected part 90. Specifically, the index value acquisition unit 2*g* acquires, as the first index value 40, a value indicating the ratio of the volume of the first superimposed region 80 to the volume of the entire affected part 90.

When performing treatment by photoimmunotherapy, it is desirable to reduce the quantity of therapeutic light emitted to parts other than the affected part 90. Therefore, in this embodiment, the index value acquisition unit 2*g* is configured to acquire a second index value 41 (see FIG. 9) that indicates the degree of superposition of the second superimposed region 82 (see FIG. 5) in which the light propagation region 31 and the parts other than the affected part 90 are superimposed. Specifically, the index value acquisition unit 2*g* acquires, as the second index value 41, a value indicating the ratio of the volume of the second superimposed region 82 to the volume of the light propagation region 31.

(Display of Composite Three-Dimensional Image, Cross-Sectional Images, First Index Value, and Second Index Value)

Figure 9:
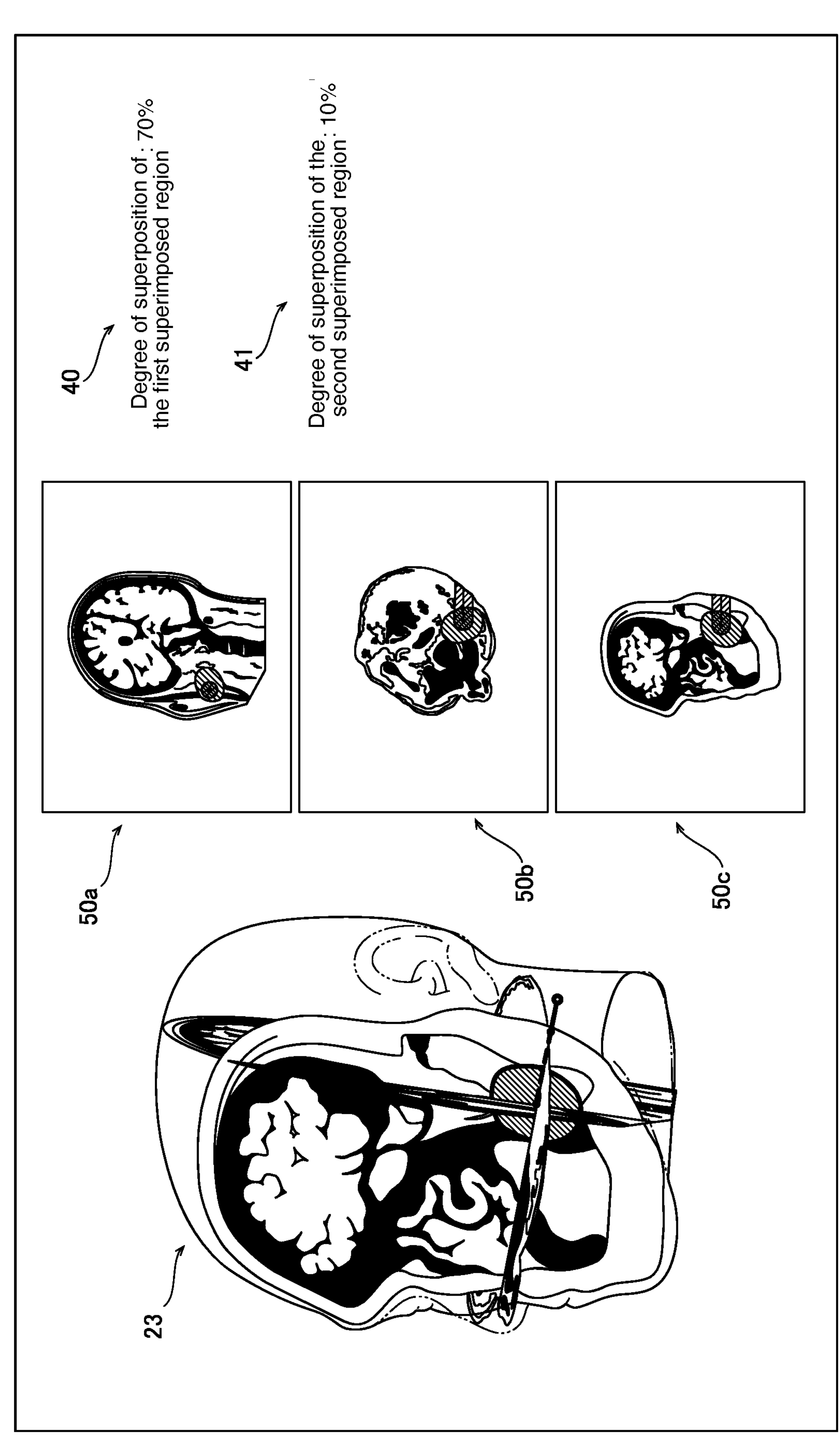
FIG. 9 is a schematic diagram for describing a configuration in which a display control unit according to one embodiment causes a composite three-dimensional image, cross-sectional images, a first index value, and a second index value to be displayed on a display unit.

Next, with reference to FIG. 9, the configuration that the display control unit 2*f* makes the display unit 4 display the composite three-dimensional image 23, the plurality of cross-sectional images 50, the first index value 40, and the second index value 41.

The display control unit 2*f* is configured to display a plurality of cross-sectional images 50 different in cross-sectional orientation from each other side by side. Specifically, the display control unit 2*f* is configured to make the display unit 4 display the cross-sectional image 50*a*, the cross-sectional image 50*b*, and the cross-sectional image 50*c* side by side. Further, in this embodiment, the display control unit 2*f* is configured to cause the composite three-dimensional image 23 to be displayed together with the plurality of cross-sectional images 50.

Further, in this embodiment, the display control unit 2*f* is configured to display the first index value 40 together with the cross-sectional images 50. Further, in this embodiment, the display control unit 2*f* is configured to display the second index value 41 together with the cross-sectional images 50.

Figure 10:
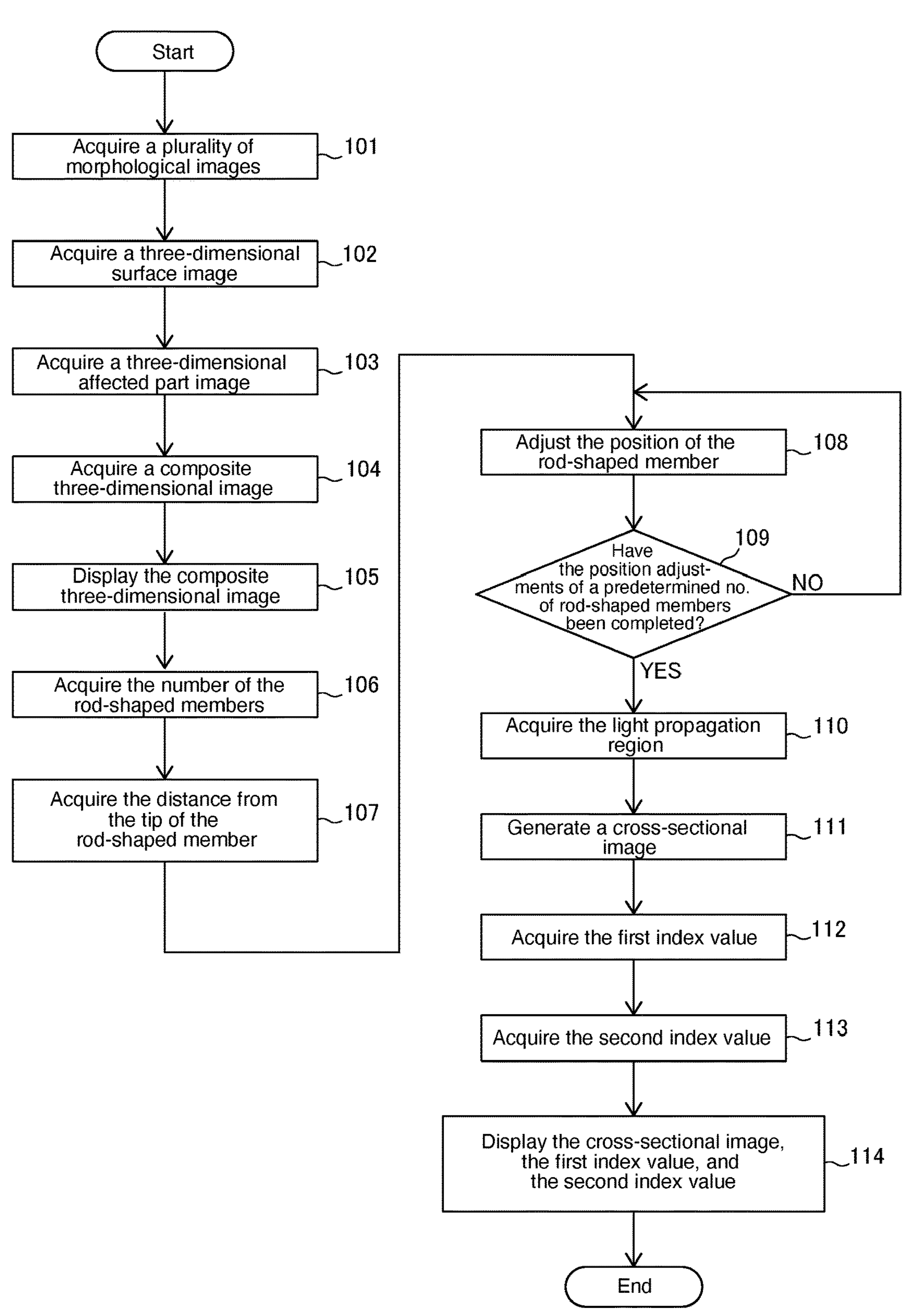
FIG. 10 is a flowchart for describing processing in which a phototherapy planning device according to one embodiment displays a cross-sectional image.

Next, referring to FIG. 10, the processing that the phototherapy planning device 100 makes the display unit 4 display the cross-sectional images 50 will be described.

In Step 101, the image acquisition unit 1 acquires a plurality of morphological images 10.

In Step 102, the three-dimensional image acquisition unit 2*b* acquires a three-dimensional surface image 20 showing the affected part 90 of the subject and the three-dimensional surface shape of the subject.

In Step 103, the three-dimensional image acquisition unit 2*b* acquires a three-dimensional affected part image 21.

In Step 104, the image composition unit 2*h* acquires a composite three-dimensional image 22. Specifically, the image composition unit 2*h* superimposes the three-dimensional surface image 20 and the three-dimensional affected part image 21 to acquire the composite three-dimensional image 22.

In Step 105, the display control unit 2*f* makes the display unit 4 display the composite three-dimensional image 22.

In Step 106, the control unit 2*a* acquires, via the input reception unit 5, the number of rod-shaped members 6 to be performed in the position adjustment. Further, the control unit 2*a* makes the storage unit 3 store the acquired number of the rod-shaped members.

In Step 107, the control unit 2*a* acquires, via the input reception unit 5, the distance 30 from the tip 6*a* of the rod-shaped members 6. In-Step 107, the control unit 2*a* acquires the distance 30 from the tip 6*a* of the rod-shaped member 6 for each rod-shaped member 6 to be performed in the position adjustment. Specifically, the control unit 2*a* acquires the distance 30 for determining the irradiation range of the light emitted from the tip 6*a* of the rod-shaped member 6. Further, the control unit 2*a* makes the storage unit 3 store the acquired distance 30 from the tip 6*a* of the rod-shaped member 6.

In Step 108, the rod-shaped member position adjustment unit 2*c* adjusts the position of the rod-shaped member 6 when inserting the rod-shaped member 6 into the affected part 90 on the image space, with respect to the three-dimensional surface image 20. Specifically, the rod-shaped member position adjustment unit 2*c* performs the position adjustment of the rod-shaped member 6 based on the position coordinate of the tip 6*a* of the rod-shaped member 6 input by the operation input and the position coordinate of the end 6*b* opposite to the tip 6*a*.

In Step 109, the control unit 2*a* determines whether the position adjustments of the predetermined number of rod-shaped members 6 have been completed. When the position adjustments of the predetermined number of rod-shaped members 6 have been completed, the processing proceeds to Step 110. In the case where the position adjustments of the predetermined number of rod-shaped members 6 have not been completed, the processing proceeds to Step 108. Note that the predetermined number of rod-shaped members denotes the number of rod-shaped members 6 to be performed in the position adjustment input in Step 106.

In Step 110, the light propagation region acquisition unit 2*d* acquires the light propagation region 31 in which light propagates from the rod-shaped member 6.

In Step 111, the cross-sectional image generation unit 2*e* generates the cross-sectional image 50 that displays the internal morphological image 60 including the affected part 90 of the subject, the rod-shaped member 6, and the light propagation region 31, in the predetermined cross section of the three-dimensional surface image 20.

In Step 112, the index value acquisition unit 2*g* acquires the first index value 40.

In Step 113, the index value acquisition unit 2*g* acquires the second index value 41.

In Step 114, the display control unit 2*f* makes the display unit 4 display the cross-sectional image 50. Note that in this embodiment, when displaying the cross-sectional images 50 on the display unit 4, the display control unit 2*f* causes the composite three-dimensional image 23, the first index value 40, and the second index value 41 to be displayed as well. Thereafter, the processing is terminated.

Note that either the processing of Step 102 or the processing of Step 103 may be performed first. Further, either the processing of Step 112 or the processing of Step 113 may be performed first.

Effects of this Embodiment

In this embodiment, the following effects can be obtained.

In this embodiment, as described above, the phototherapy planning device 100 is provided with: a three-dimensional image acquisition unit 2*b* configured to acquire a three-dimensional surface image 20 showing an affected part 90 of a subject and a three-dimensional surface shape of the subject; a rod-shaped member position adjustment unit 2*c* configured to adjust a position of the rod-shaped member 6 when inserting the rod-shaped member 6 into the affected part 90 on an image space, with respect to the three-dimensional surface image 20; a light propagation region acquisition unit 2*d* configured to acquire the light propagation region 31 in which light propagates from the rod-shaped member 6; a cross-sectional image generation unit 2*e* configured to generate a cross-sectional image 50 that displays the internal morphological image 60 including the affected part 90 of the subject, the rod-shaped member 6, and the light propagation region 31, in a predetermined cross-section of the three-dimensional surface image 20; and a display control unit 2*f* configured to perform control for displaying the cross-sectional image 50.

It is provided with a rod-shaped member position adjustment unit 2*c* for adjusting the position of the rod-shaped member 6 when inserting the rod-shaped member 6 into the affected part 90 on the image space, with respect to the three-dimensional surface image 20. Therefore, it is possible to perform the position adjustment of the rod-shaped member 6 on the image space of the three-dimensional surface image 20 showing the affected part 90. Thus, the operator can perform the position adjustment of the rod-shaped member 6 while confirming the rod-shaped member 6 on the image space of the three-dimensional surface image 20. Further, it is provided with a light propagation region acquisition unit 2*d* for acquiring the light propagation region 31 in which light propagates from the rod-shaped member 6, a cross-sectional image generation unit 2*e* for generating a cross-sectional image 50 that displays the internal morphological image 60 including an affected part 90 of a subject, the rod-shaped member 6, and the light propagation region 31, at a predetermined cross-section of the three-dimensional surface image 20, and a display control unit 2*f* for performing control to cause the cross-sectional image 50 to be displayed. Therefore, an operator can confirm the light propagation region 31 which is a region of light emitted from the rod-shaped member 6 by confirming the cross-sectional image 50 displaying the internal morphological image 60 including the affected part 90 of the subject, the rod-shaped member 6, and the light propagation region 31. As a result, it is possible to provide a phototherapy planning device 100 capable of accurately grasping the placement of the rod-shaped member 6 with respect to the affected part 90 and also capable of grasping in advance the irradiation range (light propagation region 31) of the therapeutic light to the affected part 90.

Further, in this embodiment, the phototherapy planning method includes a step of acquiring a three-dimensional surface image 20 showing the affected part 90 of the subject and the three-dimensional surface shape of the subject, a step of adjusting a position of the rod-shaped member 6 when inserting the rod-shaped member 6 into the affected part 90 on the image space, with respect to the three-dimensional surface image 20, a step of acquiring a light propagation region 31 in which light propagates from the rod-shaped member 6, a step of generating the internal morphological image 60 including the affected part 90 of the subject, the rod-shaped member 6, and the light propagation region 31 in a predetermined cross-section of the three-dimensional surface image 20, and a step of displaying the cross-sectional image 50.

With this, as with the phototherapy planning device 100, it is possible to provide a phototherapy planning method capable of accurately grasping the placement of the rod-shaped member 6 with respect to the affected part 90 and also capable of grasping in advance the irradiation range of the therapeutic light (light propagation region 31) to the affected part 90.

Further, in the above-described embodiment, the following further effects can be obtained by configuring as follows.

That is, in this embodiment, as described above, the cross-sectional image generation unit **2*e* is configured to generate, as the cross-sectional image 50, an image capable of identifying the first superimposed region 80 in which the affected part 90 and the light propagation region 31 are superimposed and the non-superimposed region 81 other than the first superimposed region 80. With this, by confirming the first superimposed region 80 in the cross-sectional image 50, it is possible to easily grasp at a glance how much the affected part 90 is irradiated with light. As a result, it is possible to easily determine whether the insertion position of the rod-shaped member 6** is appropriate.

Further, in this embodiment, as described above, it is further provided with an index value acquisition unit **2*g* that acquires the first index value 40 indicating the degree of superposition of the first superimposed region 80 with respect to the affected part 90, and the display control unit 2*f* is configured to cause the first index value 40 to be displayed together with the cross-sectional image 50. With this, it is possible not only to visually confirm the first superimposed region 80 but also to grasp, as numerical information, how much the affected part 90 is irradiated with the therapeutic light, by means of the first index value 40. As a result, it is possible to easily determine whether the insertion position of the rod-shaped member 6** is appropriate.

Further, in this embodiment, as described above, as described above, it is further provided with the input reception unit 5 for accepting the operator's operation input, and the rod-shaped member position adjustment unit **2*c* is configured to adjust the position of the rod-shaped member 6 on the image space, based on the operation input received by the input reception unit 5. With this, it is possible to intuitively perform the position adjustment of the rod-shaped member 6 on the image space. As a result, the position adjustment of the rod-shaped member 6** can be performed intuitively and easily.

Further, in this embodiment, as described above, the light propagation region acquisition unit **2*d* is configured to acquire, as the light propagation region 31, the region in which the light emitted radially outward from the center of the shaft portion 6*c* of the rod-shaped member 6 inserted into the subject out of the rod-shaped member 6 over the entire circumference of the rod-shaped member 6 propagates. With this, the light propagation region 31** can be easily obtained without using, e.g., a light diffusion equation.

Further, in this embodiment, as described above, the light propagation region acquisition unit **2*d* is configured to acquire the light propagation region 31 based on the distance 30 from the tip 6*a* of the rod-shaped member 6 input in advance and the position of the tip 6*a* of the rod-shaped member 6. With this, it is possible to easily acquire the light propagation region 31 based on the distance 30 from the tip 6*a* of the rod-shaped member 6 and the position of the tip 6*a* of the rod-shaped member 6**.

Further, in this embodiment, as described above, the three-dimensional image acquisition unit **2*b* is configured to acquire the three-dimensional affected part image 21, which is a three-dimensional image of the affected part 90, and is further provided with the image composition unit 2*h* for generating the composite three-dimensional image 22 capable of identifying the three-dimensional affected part image 21 by composing the three-dimensional surface image 20 and the three-dimensional affected part image 21. With this, it is possible to perform the position adjustment of the rod-shaped member 6 in a state in which the three-dimensional position of the affected part 90 is grasped when performing the position adjustment of the rod-shaped member 6*e* on the image space of the three-dimensional surface image 20. As a result, the position adjustment of the rod-shaped member 6** can be performed easily.

Further, in this embodiment, as described above, the cross-sectional image generation unit **2*e* is configured to generate, as the cross-sectional image 50, an image capable of distinguishing the affected part 90 from other parts other than the affected part 90. With this, in the cross-sectional image 50, the affected part 90 and other parts other than the affected part 90 can be easily distinguished. As a result, it is possible to perform treatment planning in a state in which the position of the affected part 90** is grasped, which can improve the accuracy of the treatment planning.

Further, in this embodiment, as described above, the cross-sectional image generation unit **2*e* is configured to generate a plurality of cross-sectional images 50 showing at least the tip 6*a* of the rod-shaped member 6, and the display control unit 2*f* is configured to cause the plurality of cross-sectional images 50 different in orientation of the cross section to be displayed side by side. With this, it is possible to confirm the light propagation region 31 by the cross-sectional images 50 with multiple orientations. As a result, it is possible to grasp whether the rod-shaped member 6 is properly positioned by the cross-sectional images 50** with multiple orientations, and therefore, the accuracy of the treatment planning can be improved.

Further, in this embodiment, as described above, the index value acquisition unit **2*g* is configured to acquire the second index value 41 that indicates the degree of superposition of the second superimposed region 82 in which the light propagation region 31 and the parts other than the affected part 90 are superimposed, and the display control unit 2***f* is configured to cause the second index value 41 to be displayed together with the cross-sectional image 50. With this, it is possible to easily grasp, as numerical information, how much the parts other than the affected part 90 are included in the light propagation region 31 by confirming the second index value 41. As a result, it is possible to grasp, as numerical information, how much a normal region is irradiated with the therapeutic light during the treatment.

Modifications

Note that the embodiments disclosed here should be considered illustrative and not restrictive in all respects. The scope of the present invention is indicated not by the above-described description of the embodiments but by claims and includes all modifications (modified examples) within the meaning and scope equivalent to the claims.

For example, in the above-described embodiment, an example of a configuration in which the image composition unit 2*h* composes the composite three-dimensional image 22 by composing the three-dimensional surface image 20 and the three-dimensional affected part image 21 is shown, but the present invention is not limited thereto. For example, as shown in FIG. 11, the image composition unit 12*b* according to the modification may be configured to generate a three-dimensional image 25 by composing the three-dimensional surface image 20, the three-dimensional affected part image 21, and the three-dimensional internal structure image 24.

Figure 11:
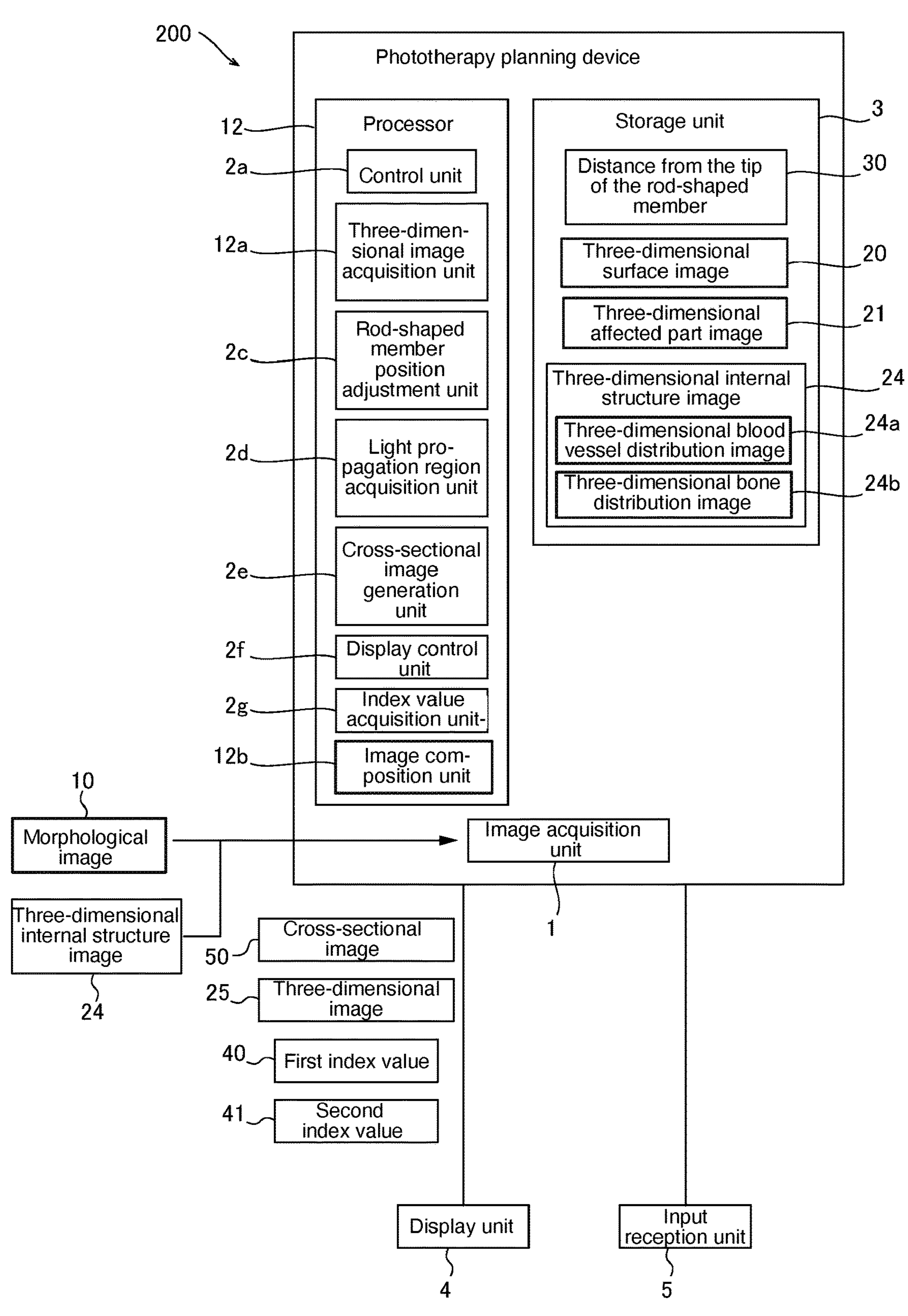
FIG. 11 is a block diagram showing an entire configuration of a phototherapy planning device according to a modification.

As shown in FIG. 11, the phototherapy planning device 200 according to the modification differs from the phototherapy planning device 100 according to the above-described embodiment in that it is provided with a processor 12 instead of the processor 2.

The processor 12 differs from the processor 2 according to the above-described embodiment in that it is provided with a three-dimensional image acquisition unit 12*a* instead of the three-dimensional image acquisition unit 2*b*, and an image composition unit 12*b* instead of the image composition unit 2*h*.

The three-dimensional image acquisition unit 12*a* according to the modification is configured to acquire the three-dimensional internal structure image 24, which is a three-dimensional image of the internal structure of the subject. Specifically, the three-dimensional image acquisition unit 12*a* according to the modification is configured to acquire, as the three-dimensional internal structure image 24, any one of the three-dimensional blood vessel distribution image 24*a* showing the three-dimensional distribution of the blood vessel 93 (see FIG. 12) of the subject and the three-dimensional bone distribution image 24*b* showing the three-dimensional distribution of the bone 94 (see FIG. 13) of the subject.

The three-dimensional image acquisition unit 12*a* according to the modification acquires the three-dimensional internal structure image 24 via the image acquisition unit 1. Specifically, the three-dimensional image acquisition unit 12*a* acquires, as a three-dimensional internal structure image 24, a three-dimensional blood vessel distribution image 24*a* or a three-dimensional bone distribution image 24*b*.

In the case of acquiring the three-dimensional blood vessel distribution image 24*a*, the three-dimensional image acquisition unit 12*a* acquires, as the three-dimensional blood vessel distribution image 24*a*, a blood vessel image (MRA image: Magnetic Resonance Angiography) showing the blood vessel 93 in the vicinity of the affected part 90, via the image acquisition unit 1.

Further, in the case of acquiring the three-dimensional bone distribution image 24*b*, the three-dimensional image acquisition unit 12*a* acquires, as the three-dimensional bone distribution image 24*b*, a CT image showing the bone 94 in the vicinity of the affected part 90, via the image acquisition unit 1.

The image composition unit 12*b* according to the modification is configured to generate, as the composite three-dimensional image 22, the three-dimensional image 25 obtained by composing the three-dimensional surface image 20, the three-dimensional affected part image 21, and the three-dimensional internal structure image 24. Specifically, the image composition unit 12*b* is configured to compose the three-dimensional surface image 20 and the three-dimensional blood vessel distribution image 24*a* (see FIG. 12) or the three-dimensional bone distribution image 24*b* (see FIG. 13).

Figure 12:
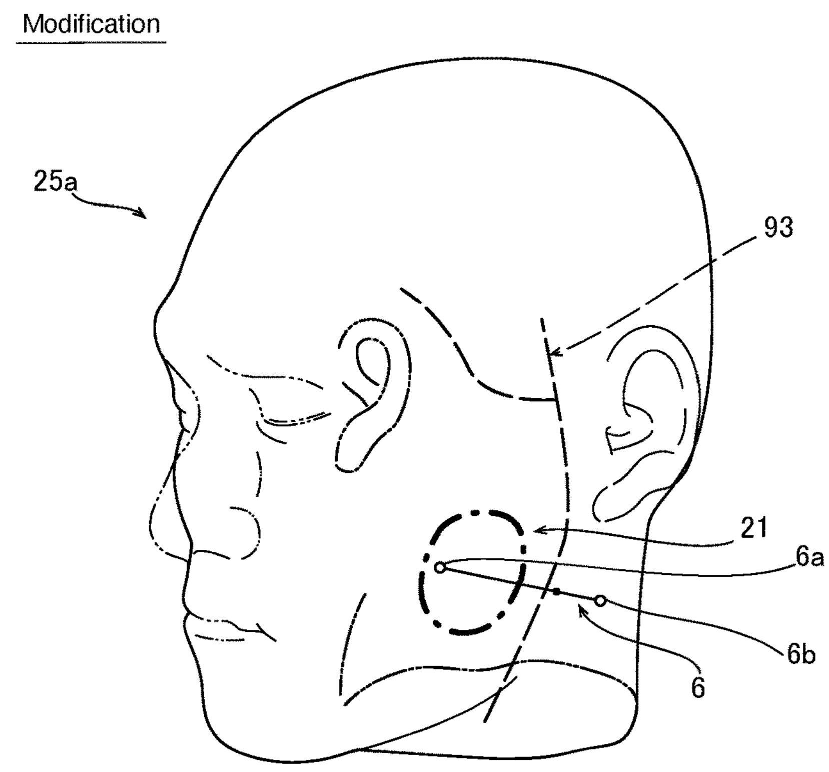
FIG. 12 is a schematic diagram for describing a composite image obtained by composing a three-dimensional surface image and a three-dimensional blood vessel distribution image obtained by a three-dimensional image acquisition unit according to a modification.

FIG. 12 is a schematic diagram of the three-dimensional image 25*a* generated by the image composition unit 12*b*. The three-dimensional image 25 is a three-dimensional image obtained by composing the three-dimensional surface image 20, the three-dimensional affected part image 21, and the three-dimensional blood vessel distribution image 24*a*. As shown in FIG. 12, in the three-dimensional image 25*a*, the blood vessels 93 is displayed together with the affected part 90 of the subject. Note that in the example shown in FIG. 12, the blood vessel 93 is illustrated with dashed lines for convenience.

Figure 13:
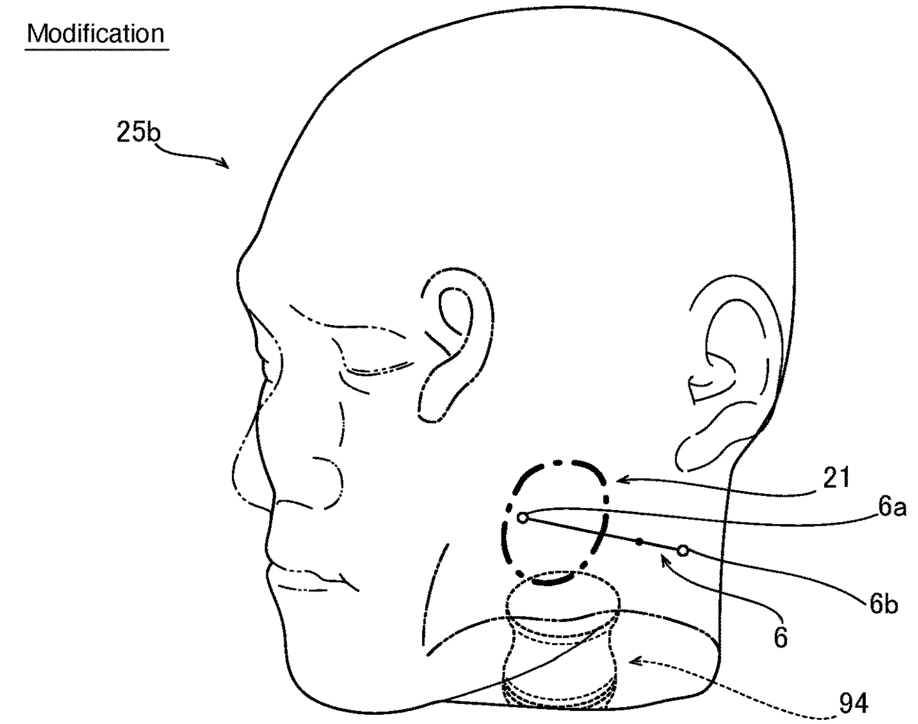
FIG. 13 is a schematic diagram for describing a composite image obtained by composing a three-dimensional surface image and a three-dimensional bone distribution image by a three-dimensional image acquisition unit according to a modification.

FIG. 13 is a schematic diagram of the three-dimensional image 25*b* generated by the image composition unit 12*b*. The three-dimensional image 25*b* is a three-dimensional image obtained by composing the three-dimensional surface image 20, the three-dimensional affected part image 21, and the three-dimensional bone distribution image 24*b*. As shown in FIG. 13, in the three-dimensional image 25*b*, the bone 94 is displayed together with the affected part 90 of the subject. Note that in the example shown in FIG. 13, the bone 94 is illustrated with dashed lines for convenience.

Figure 14:
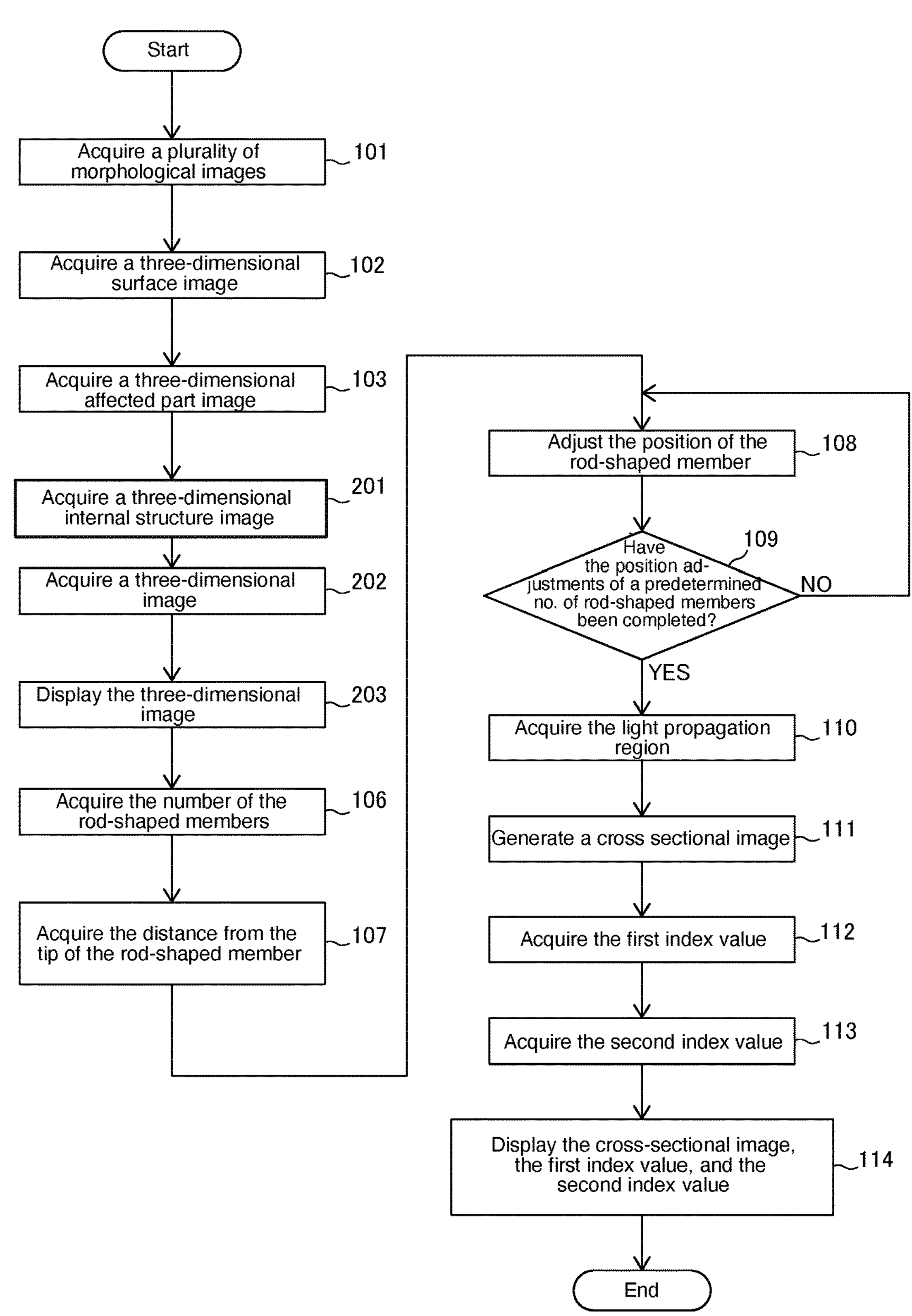
FIG. 14 is a flowchart for describing processing in which a phototherapy planning device according to a modification displays a cross-sectional image.

Next, referring to FIG. 14, the processing that the phototherapy planning device 200 according to the modification causes the cross-sectional image 50 to be displayed will be described. Note that the same processing as the processing that the phototherapy planning device 100 according to the above-described embodiment causes the cross-sectional image 50 to be displayed is assigned by the same reference symbol, and the detailed explanation thereof will be omitted.

In Steps 101 to 103, the three-dimensional image acquisition unit 12*a* acquires the three-dimensional surface image 20 and the three-dimensional affected part image 21.

In Step 201, the three-dimensional image acquisition unit 12*a* acquires the three-dimensional internal structure image 24. Note that in this embodiment, the three-dimensional image acquisition unit 12*a* acquires, as the three-dimensional internal structure image 24, the three-dimensional blood vessel distribution image 24*a* or the three-dimensional bone distribution image 24*b*.

In Step 202, the image composition unit 12*b* composes the three-dimensional surface image 20, the three-dimensional affected part image 21, and the three-dimensional internal structure image 24 to obtain the three-dimensional image 25.

In Step 203, the display control unit 2*f* makes the display unit 4 display the three-dimensional image 25.

Thereafter, the processing proceeds to Step 106 to Step 114, and then is terminated.

In the modification, as described above, the three-dimensional image acquisition unit 2*b* is configured to acquire the three-dimensional internal structure image 24, which is a three-dimensional image of the internal structure of the subject. The image composition unit 2*h* is configured to generate, as the composite three-dimensional image 22, the three-dimensional image 25 obtained by composing the three-dimensional surface image 20, the three-dimensional affected part image 21, and the three-dimensional internal structure image 24. With this, it is possible to grasp the three-dimensional position of the affected part 90 and the internal structure of the subject when adjusting the insertion position of the rod-shaped member 6 on the image space of the three-dimensional image 25. As a result, the operator can grasp the position of the internal structure of the subject that must be avoided when placing the rod-shaped member 6, while grasping the position of the affected part 90 when performing the position adjustment of the rod-shaped member 6 on the image space of the three-dimensional image 25.

Further, in the modification, as described above, the three-dimensional image acquisition unit 2*b* is configured to acquire, as the three-dimensional internal structure image 24, any one of the three-dimensional blood vessel distribution image 24*a* showing the three-dimensional distribution of the subject's blood vessels 93 and the three-dimensional bone distribution image 24*b* showing the three-dimensional distribution of the subject's bone 94. The image composition unit 2*h* is configured to compose the three-dimensional surface image 20 and the three-dimensional blood vessel distribution image 24*a* or the three-dimensional bone distribution image 24*b*. With this, in the three-dimensional image 25, it is possible to grasp the distribution of the affected parts 90 as well as the distribution of the blood vessel 93 or the distribution of the bones 94. As a result, when inserting the rod-shaped member 6, it is possible to grasp the position of the blood vessel 93 to be avoided or the position of the bone 94 that obstructs the insertion of the rod-shaped member 6, and therefore, it is possible to perform more accurate treatment planning.

Further, in the above-described embodiment, an example of a configuration in which the image composition unit 2*h* displays the three-dimensional surface image 20 and the three-dimensional affected part image 21 in a distinguishable manner by highlighting the border of the three-dimensional affected part image 21 is shown, but the present invention is not limited thereto. Specifically, the image composition unit 2*h* differentiates the display mode of the three-dimensional surface image 20 from that of the three-dimensional affected part image 21 to cause the three-dimensional surface image 20 and the three-dimensional affected part image 21 to be displayed in a distinguishable manner. Further, the image composition unit 2*h* may display the three-dimensional surface image 20 and the three-dimensional affected part image 21 in a distinguishable manner by differentiating the intensity of the display color of the three-dimensional surface image 20 from that of the three-dimensional affected part image 21. As long as the three-dimensional surface image 20 and the three-dimensional affected part image 21 are distinguishable, the image composition unit 2*h* may display the three-dimensional surface image 20 and the three-dimensional affected part image 21 in any manner.

Further, in the above-described embodiment, an example of a configuration in which the cross-sectional image generation unit 2*e* generates, as the cross-sectional image 50, an image capable of identifying the first superimposed region 80 and a non-superimposed region 81 other than the first superimposed region 80 is shown, but the present invention is not limited thereto. For example, the cross-sectional image generation unit 2*e* may be configured to generate an image in which the first superimposed region 80 and the non-superimposed region 81 are not distinguishable as long as the internal morphological image 60, the rod-shaped member 6, and the light propagation region 31 are displayed in the cross-sectional image 50.

Further, in the above-described embodiment, an example of a configuration in which the phototherapy planning device 100 is provided with the index value acquisition unit 2*g*, and the index value acquisition unit 2*g* acquires the first index value 40 and the second index value 41 is shown, but the present invention is not limited thereto. For example, the phototherapy planning device 100 may not be provided with the index value acquisition unit 2*g*. However, in the case where the phototherapy planning device 100 is not provided with the index value acquisition unit 2*g*, the operator cannot grasp the first index value 40 and the second index value 41. Therefore, the phototherapy planning device 100 is preferably provided with the index value acquisition unit 2*g*.

Further, in the above-described embodiment, an example of a configuration in which the light propagation region acquisition unit 2*d* acquires the light propagation region 31 based on the position of the tip 6*a* of the rod-shaped member 6 and the distance 30 from the tip 6*a* of the rod-shaped member 6 is shown, but the present invention is not limited thereto. For example, the light propagation region acquisition unit 2*d* may be configured to acquire the light propagation region 31 based on a light diffusion equation or the like. The light propagation region acquisition unit 2*d* may be configured to acquire the light propagation region 31 in any manner as long as it is possible to acquire the light propagation region 31.

Further, in the above-described embodiment, an example of a configuration in which the phototherapy planning device 100 is provided with the image composition unit 2*h*, and the image composition unit 2*h* generates the composite three-dimensional image 22 obtained by composing the three-dimensional surface image 20 and the three-dimensional affected part image 21 is shown, but the present invention is not limited thereto. For example, the phototherapy planning device 100 may not be provided with the image composition unit 2*h*. In the case where the phototherapy planning device 100 is not equipped with the image composition unit 2*h*, the three-dimensional image acquisition unit 2*b* may be configured to acquire a composite three-dimensional image 22 generated by an image processing unit different from the phototherapy planning device 100.

Further, in the above-described embodiment, an example of a configuration in which the cross-sectional image generation unit 2*e* displays the affected part 90 and other parts other than the affected part 90 in a distinguishable manner by differentiating the display color of the affected part 90 from that of the other parts of the image, but the present invention is not limited thereto. For example, the cross-sectional image generation unit 2*e* may highlight the border of the affected part 90 to thereby display the affected part 90 and other parts other than the affected part 90 in a distinguishable manner. Further, the cross-sectional image generation unit 2*e* may display the affected part 90 and other parts other than the affected part 90 in a distinguishable manner by differentiating the intensity of the display color of the affected part 90 from the intensity of the display color of other parts other than the affected part 90. As long as the affected part 90 and other parts other than the affected part 90 are displayed in an identifiable manner, the cross-sectional image generation unit 2*e* may display the affected part 90 and other parts other than the affected part 90 in any manner.

Further, in the above-described embodiment, an example of a configuration in which the cross-sectional image generation unit 2*e* generates, as the cross-sectional image 50, an image capable of distinguishing between the affected part 90 and other parts other than the affected part 90 is shown, but the present invention is not limited thereto. For example, the cross-sectional image generation unit 2*e* may be configured to generate, as the cross-sectional image 50, an image not capable of distinguishing between the affected part 90 and parts other than the affected part 90. However, in the case where the affected part 90 and parts other than the affected part 90 are not distinguishable in the cross-sectional image 50, it may be difficult to determine whether the position of the rod-shaped member 6 is correct. This reduces the accuracy of treatment planning. Therefore, the cross-sectional image generation unit 2*e* is preferably configured to generate, as the cross-sectional image 50, an image capable of distinguishing between the affected part 90 and parts other than the affected part 90.

Further, in the above-described embodiment, an example of a configuration in which the cross-sectional image generation unit 2*e* generates a plurality of cross-sectional images 50, and the display control unit 2*f* causes the plurality of cross-sectional images 50 different in cross-sectional orientation from each other to be displayed side by side is shown, but the present invention is not limited thereto. For example, the cross-sectional image generation unit 2*e* may be configured to generate a single cross-sectional image 50. Further, the display control unit 2*f* may be configured to cause a single cross-sectional image 50 to be displayed. However, it is possible for the operator to grasp the light propagation region 31 in more detail in a configuration that a plurality of cross-sectional images 50 different in cross-sectional orientation is displayed. Therefore, the cross-sectional image generation unit 2*e* is preferably configured to generate a plurality of cross-sectional images 50. Further, the display control unit 2*f* is preferably configured to cause a plurality of cross-sectional images 50 to be displayed.

Further, in the above-described embodiment, an example of a configuration in which the three-dimensional image acquisition unit 2*b* generates the three-dimensional surface image 20 based on the plurality of morphological images 10 is shown, but the present invention is not limited thereto. For example, the three-dimensional image acquisition unit 2*b* may be configured to acquire the three-dimensional surface image 20 generated in advance by an image processor or other device different from the phototherapy planning device 100. Further, the three-dimensional image acquisition unit 2*b* may be configured to acquire the voxel data of the three-dimensional surface image 20.

Further, in the above-described embodiment, an example of a configuration in which the three-dimensional image acquisition unit 2*b* acquires the three-dimensional affected part image 21 based on a plurality of slice images showing the affected part 90 is shown, but the present invention is not limited thereto. For example, the three-dimensional image acquisition unit 2*b* may be configured to acquire the three-dimensional affected part image 21 generated in advance by an image processor or other device different from the phototherapy planning device 100. Further, the three-dimensional image acquisition unit 2*b* may be configured to acquire, as the three-dimensional affected part image 21, an image taken by a PET (Positron Emission Tomography) or the like. Further, the three-dimensional image acquisition unit 2*b* may be configured to acquire the three-dimensional affected part image 21 as voxel data.

Further, in the above-described embodiment, an example of a configuration in which the light propagation region acquisition unit 2*d* acquires the light propagation region 31 upon completion of the position adjustments of the predetermined number of rod-shaped members 6, but the present invention is not limited thereto. For example, the light propagation region acquisition unit 2*d* may be configured to acquire the light propagation region 31 when an operation input to start acquisition of the light propagation region 31 is made by the operator, even before completion of the position adjustments of the predetermined number of rod-shaped members 6.

Further, in the above-described embodiment, an example of a configuration in which the cross-sectional image generation unit 2*e* differentiates the display color of the light propagation region 31 from that of the affected part 90 to display the light propagation region 31 and the affected part 90 in a distinguishable manner is shown, but the present invention is not limited thereto. For example, the cross-sectional image generation unit 2*e* may highlight the border of the light propagation region 31 to display the light propagation region 31 and the affected part 90 in a distinguishable manner. Further, the cross-sectional image generation unit 2*e* may differentiate the intensity of the display color of the light propagation region 31 from that of the affected part 90 to display the light propagation region 31 and the affected part 90 in a distinguishable manner. The cross-sectional image generation unit 2*e* may display the light propagation region 31 and the affected part 90 in any manner as long as the light propagation region 31 and the affected part 90 are displayed in an identifiable manner.

Further, in the above-described embodiment, an example of a configuration in which the cross-sectional image generation unit 2*e* differentiates the display color of the first superimposed region 80 from that of the non-superimposed region 81 to display the first superimposed region 80 and the non-superimposed region 81 in a distinguishable manner is shown, but the present invention is not limited thereto. For example, the cross-sectional image generation unit 2*e* may highlight the border of the first superimposed region 80 to display the first superimposed region 80 and the non-superimposed region 81 in a distinguishable manner. Further, the cross-sectional image generation unit 2*e* may differentiate the intensity of the display color of the first superimposed region 80 from that of the display color of the non-superimposed region 81 to display the first superimposed region 80 and the non-superimposed region 81 in a distinguishable manner. The cross-sectional image generation unit 2*e* may display the first superimposed region 80 and the non-superimposed region 81 in any manner as long as the first superimposed region 80 and the non-superimposed region 81 are displayed in an identifiable manner.

Further, in the above-described embodiment, an example of a configuration in which the cross-sectional image generation unit 2*e* differentiates the display color of the first superimposed region 80 from that of the second superimposed region 82 to display the first superimposed region 80 and the second superimposed region 82 in a distinguishable manner is shown, but the present invention is not limited thereto. For example, the cross-sectional image generation unit 2*e* may highlight the border of the first superimposed region 80 to display the first superimposed region 80 and the second superimposed region 82 in a distinguishable manner. Further, the cross-sectional image generation unit 2*e* may differentiate the intensity of the display color of the first superimposed region 80 from that of the display color of the second superimposed region 82 to display the first superimposed region 80 and the second superimposed region 82 in a distinguishable manner. The cross-sectional image generation unit 2*e* may display the first superimposed region 80 and the second superimposed region 82 in any manner as long as the first superimposed region 80 and the second superimposed region 82 are displayed in an identifiable manner.

Further, in the above-described embodiment, an example of a configuration in which the three-dimensional image acquisition unit 2*b* acquires the three-dimensional surface image 20 in which the inside is hollow is shown, but the present invention is not limited thereto. For example, the three-dimensional image acquisition unit 2*b* may be configured to acquire a three-dimensional image including the internal morphological image 60, instead of acquiring the three-dimensional surface image 20.

Further, in the above-described embodiment, an example of a configuration in which the phototherapy planning device 100 is provided with the three-dimensional image acquisition unit 2*b*, the rod-shaped member position adjustment unit 2*c*, the light propagation region acquisition unit 2*d*, and the cross-sectional image generation unit 2*e* is shown, but the present invention is not limited thereto. For example, the phototherapy planning device 100 may not be provided with the three-dimensional image acquisition unit 2*b*, the rod-shaped member position adjustment unit 2*c*, the light propagation region acquisition unit 2*d*, and the cross-sectional image generation unit 2*e*. That is, it may be configured such that the three-dimensional image acquisition unit 2*b*, the rod-shaped member position adjustment unit 2*c*, the light propagation region acquisition unit 2*d*, and the cross-sectional image generation unit 2*e* are provided on a server, such as, e.g., an HIS (Hospital Information System) server and an RIS (Radiology Information Systems) server, and the phototherapy planning device acquires the cross-sectional image 50 generated by a server, such as, e.g., an HIS server and an RIS server, via a network and displays it on the display unit 4. In other words, the phototherapy planning device 100 may be configured as a part of a so-called client-server system.

Aspect

It would be understood by those skilled in the art that the exemplary embodiments described above are specific examples of the following aspects.

Item 1

A phototherapy planning device includes:

a three-dimensional image acquisition unit configured to acquire a three-dimensional surface image showing an affected part of a subject and a three-dimensional surface shape of the subject;

a rod-shaped member position adjustment unit configured to adjust a position of a rod-shaped member when inserting the rod-shaped member into the affected part on an image space, with respect to the three-dimensional surface image;

a light propagation region acquisition unit configured to acquire a light propagation region in which light propagates from the rod-shaped member;

a cross-sectional image generation unit configured to generate a cross-sectional image that displays, in a predetermined cross-section of the three-dimensional surface image, an internal morphological image including the affected part of the subject, the rod-shaped member, and the light propagation region; and a display control unit configured to perform control for displaying the cross-sectional image.

Item 2

The phototherapy planning device as recited in the above-described Item 1, wherein the cross-sectional image generation unit is configured to generate, as the cross-sectional image, an image that can identify a first superimposed region in which the affected part and the light propagation region are overlapped and a non-superimposed region other than the first superimposed region.

Item 3

The phototherapy planning device as recited in the above-described Item 2, further includes:

an index value acquisition unit configured to acquire a first index value indicating a degree of superposition of the first superimposed region with respect to the affected part, wherein the display control unit is configured to cause the first index value to be displayed together with the cross-sectional image.

Item 4

The phototherapy planning device as recited in the above-described Item 1, further includes:

an input reception unit configured to receive an operation input of an operator, wherein the rod-shaped member position adjustment unit is configured to adjust the position of the rod-shaped member in the image space, based on the operation input received by the input reception unit.

Item 5

The phototherapy planning device as recited in the above-described Item 1, wherein the light propagation region acquisition unit is configured to acquire, as the light propagation region, a region in which light emitted radially outward from a center of a shaft portion of the rod-shaped member inserted into the subject out of the rod-shaped member over an entire circumference of the rod-shaped member propagates.

Item 6

The phototherapy planning device as recited in the above-described Item 5, wherein the light propagation region acquisition unit is configured to acquire the light propagation region, based on a distance from a tip of the rod-shaped member input in advance and a position of the tip of the rod-shaped member.

Item 7

The phototherapy planning device as recited in the above-described Item 1, wherein the three-dimensional image acquisition unit is configured to acquire a three-dimensional affected part image which is a three-dimensional image of the affected part, and wherein the phototherapy planning device is further provided with an image composition unit configured to compose the three-dimensional surface image and the three-dimensional affected part image to generate a composite three-dimensional image capable of identifying the three-dimensional affected part image.

Item 8

The phototherapy planning device as recited in the above-described Item 7, wherein the three-dimensional image acquisition unit is configured to acquire a three-dimensional internal structure image which is a three-dimensional image of an internal structure of the subject, and wherein the image composition unit is configured to generate, as the composite three-dimensional image, a three-dimensional image in which the three-dimensional surface image, the three-dimensional affected part image, and the three-dimensional internal structure image are combined.

Item 9

The phototherapy planning device as recited in the above-described Item 8, wherein the three-dimensional image acquisition unit is configured to acquire, as the three-dimensional internal structure image, either a three-dimensional blood vessel distribution image showing a three-dimensional distribution of a blood vessel of the subject or a three-dimensional bone distribution image showing a three-dimensional distribution of a bone of the subject, and wherein the image composition unit is configured to compose the three-dimensional surface image and either the three-dimensional blood vessel distribution image or the three-dimensional bone distribution image.

Item 10

The phototherapy planning device as recited in the above-described Item 1, wherein the cross-sectional image generation unit is configured to generate, as the cross-sectional image, an image capable of distinguishing between the affected part and other parts of the body other than the affected part.

Item 11

The phototherapy planning device as recited in the above-described Item 1, wherein the cross-sectional image generation unit is configured to generate a plurality of the cross-sectional images each showing at least the tip of the rod-shaped member, and wherein the display control unit is configured to display the plurality of the cross-sectional images side by side, the plurality of the cross-sectional images being different in cross-sectional orientation from each other.

Item 12

The phototherapy planning device as recited in the above-described Item 3, wherein the index value acquisition unit is configured to acquire a second index value indicating a degree of superposition of a second superimposed region in which the light propagation region and a part other than the affected part are superimposed, and wherein the display control unit is configured to cause the second index value to be displayed together with the cross-sectional image.

Item 13

A phototherapy planning method comprising:

a step of acquiring a three-dimensional surface image showing an affected part of a subject and a three-dimensional surface shape of the subject;

a step of adjusting a position of a rod-shaped member when inserting the rod-shaped member into the affected part on an image space, with respect to the three-dimensional surface image;

a step of acquiring a light propagation region in which light propagates from the rod-shaped member;

a step of generating a cross-sectional image that displays, in a predetermined cross-section of the three-dimensional surface image, an internal morphological image including the affected part of the subject, the rod-shaped member, and the light propagation region; and a step of causing the cross-sectional image to be displayed.

BRIEF DESCRIPTION OF REFERENCE SYMBOL

2*b*, 12*a*: Three-dimensional image acquisition unit
2*c*: Rod-shaped member position adjustment unit
2*d*: Light propagation region acquisition unit
2*e*: Cross-sectional image generation unit
2*f*: Display control unit
2*g*: Index value acquisition unit
2*h*, 12*b*: Image generation unit
5: Input reception unit
6: Rod-shaped member
6*a*: Tip of a rod-shaped member
6*c*: Shaft portion of a rod-shaped member
20: Three-dimensional surface image
21: Three-dimensional affected part image
22, 23: Composite three-dimensional image
24: Three-dimensional internal structure image
24*a*: Three-dimensional blood vessel distribution image
24*b*: Three-dimensional bone distribution image
25, 25*a*, 25*b*: Three-dimensional images (composite three-dimensional surface image obtained by composing a three-dimensional surface image, a three-dimensional affected part image, and a three-dimensional internal structure image)
30: Distance from the tip 6*a* of the rod-shaped member 6
31: Light propagation region
40: First index value
41: Second index value
50, 50*a*, 50*b*, 50*c*: Cross sectional image
60: Internal morphological image
80: First superimposed region
81: Non-superimposed region
82: Second superimposed region

90: Affected part

100, 200: Phototherapy planning device

The invention claimed is:

1. A phototherapy planning device comprising:

a memory that stores instructions;

an input receptor configured to receive an operation input of an operator; and a processor that executes the instructions stored in the memory to:

acquire a CT image or an MRI image;

generate a three-dimensional image including an affected part of a subject and a three-dimensional surface shape of the subject based on the acquired CT image or the acquired MRI image;

adjust a position of a rod-shaped member with respect to the three-dimensional image on an image space based on the operation input of the operator received by the input receptor;

acquire a light propagation region in which light propagates radially relative to an axial direction of the rod-shaped member;

generate a cross-sectional image that displays, in a predetermined cross-section of the three-dimensional image, an internal morphological image including the affected part of the subject, the rod-shaped member, and the light propagation region; and display the cross-sectional image.

2. The phototherapy planning device as recited in claim 1, wherein the processor is configured to generate, as the cross-sectional image, an image capable of identifying a first superimposed region in which the affected part and the light propagation region are superimposed and a non-superimposed region other than the first superimposed region.

3. The phototherapy planning device as recited in claim 2, wherein the processor is configured to:

acquire a first index value indicating a degree of superposition of the first superimposed region with respect to the affected part; and cause the first index value to be displayed together with the cross-sectional image.

4. The phototherapy planning device as recited in claim 3, wherein the processor is configured to:

acquire a second index value indicating a degree of superposition of a second superimposed region in which the light propagation region and a part other than the affected part are superimposed, and cause the second index value to be displayed together with the cross-sectional image.

5. The phototherapy planning device as recited in claim 1, wherein the processor is configured to acquire, as the light propagation region, a region in which light emitted radially outward from a center of a shaft portion of the rod-shaped member inserted into the subject out of the rod-shaped member over an entire circumference of the rod-shaped member propagates.

6. The phototherapy planning device as recited in claim 5, wherein the processor is configured to acquire the light propagation region, based on a distance from a tip of the rod-shaped member input in advance and a position of the tip of the rod-shaped member.

7. The phototherapy planning device as recited in claim 1, wherein the processor is configured to:

acquire the three-dimensional image showing the three-dimensional surface shape of the subject based on the CT image or the MRI image, acquire a three-dimensional affected part image which is a three-dimensional image of the affected part, and compose the three-dimensional image and the three-dimensional affected part image to generate a composite three-dimensional image capable of identifying the three-dimensional affected part image as the three-dimensional image.

8. The phototherapy planning device as recited in claim 7, wherein the processor is configured to:

acquire a three-dimensional internal structure image which is a three-dimensional image of an internal structure of the subject, and generate, as the composite three-dimensional image, a three-dimensional image in which the three-dimensional image, the three-dimensional affected part image, and the three-dimensional internal structure image are combined.

9. The phototherapy planning device as recited in claim 8, wherein the processor is configured to:

acquire, as the three-dimensional internal structure image, either a three-dimensional blood vessel distribution image showing a three-dimensional distribution of a blood vessel of the subject or a three-dimensional bone distribution image showing a three-dimensional distribution of a bone of the subject, and compose the three-dimensional image and either the three-dimensional blood vessel distribution image or the three-dimensional bone distribution image.

10. The phototherapy planning device as recited in claim 1, wherein the processor is configured to generate, as the cross-sectional image, an image capable of distinguishing between the affected part and other parts of the subject other than the affected part.

11. The phototherapy planning device as recited in claim 1, wherein the processor is configured to:

generate a plurality of cross-sectional images, each cross-sectional image of the plurality of the cross-sectional images showing at least a tip of the rod-shaped member, and display each cross-sectional image of the plurality of the cross-sectional images side by side, each cross-sectional image of the plurality of the cross-sectional images being different in cross-sectional orientation from each other.

12. The phototherapy planning device of claim 1, wherein the processor executes the instructions stored in the memory to acquire the light propagation region in which light propagates from the rod-shaped member in advance of emitting light from the rod-shaped member on the subject.

13. A phototherapy planning method comprising:

a step of acquiring a CT image or an MRI image;

a step of generating a three-dimensional image including an affected part of a subject and a three-dimensional surface shape of the subject based on the acquired CT image or the acquired MRI image;

a step of receiving an operation input of an operator;

a step of adjusting a position of a rod-shaped member with respect to the three-dimensional image on an image space based on the operation input of the operator received by an input receptor;

a step of acquiring a light propagation region in which light propagates radially relative to an axial direction of the rod-shaped member;

a step of generating a cross-sectional image that displays, in a predetermined cross-section of the three-dimensional image, an internal morphological image including the affected part of the subject, the rod-shaped member, and the light propagation region; and a step of causing the cross-sectional image to be displayed.

14. The phototherapy planning method of claim 13, wherein the step of acquiring the light propagation region in which light propagates from the rod-shaped member is performed in advance of emitting light from the rod-shaped member on the subject.

* * * * *